(12) United States Patent
Kirshner et al.

(10) Patent No.: US 12,091,460 B2
(45) Date of Patent: Sep. 17, 2024

(54) USE OF BISPECIFIC ANTIGEN-BINDING MOLECULES THAT BIND MUC16 AND CD3 IN COMBINATION WITH 4-1BB CO-STIMULATION

(71) Applicant: REGENERON PHARMACEUTICALS, INC., Tarrytown, NY (US)

(72) Inventors: Jessica R. Kirshner, New York, NY (US); Alison Crawford, Dobbs Ferry, NY (US); Danica Chiu, London (GB)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 695 days.

(21) Appl. No.: 16/906,634

(22) Filed: Jun. 19, 2020

(65) Prior Publication Data
US 2020/0399371 A1    Dec. 24, 2020

Related U.S. Application Data

(60) Provisional application No. 62/864,960, filed on Jun. 21, 2019.

(51) Int. Cl.
| | |
|---|---|
| C07K 16/46 | (2006.01) |
| A61B 6/00 | (2006.01) |
| A61B 6/03 | (2006.01) |
| A61K 51/10 | (2006.01) |
| C07K 16/28 | (2006.01) |
| C07K 16/30 | (2006.01) |
| A61K 39/00 | (2006.01) |

(52) U.S. Cl.
CPC .......... *C07K 16/2809* (2013.01); *A61B 6/037* (2013.01); *A61B 6/481* (2013.01); *A61K 51/1042* (2013.01); *C07K 16/2878* (2013.01); *C07K 16/3092* (2013.01); *A61K 2039/507* (2013.01); *C07K 2317/31* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 5,639,879 | A | 6/1997 | Mease et al. |
| 5,821,337 | A | 10/1998 | Carter et al. |
| 6,596,541 | B2 | 7/2003 | Murphy et al. |
| 7,087,411 | B2 | 8/2006 | Daly et al. |
| 8,586,713 | B2 | 11/2013 | Davis et al. |
| 10,143,186 | B2 | 12/2018 | McWhirter et al. |
| 10,179,819 | B2 | 1/2019 | Kirshner et al. |
| 2009/0142354 | A1 | 6/2009 | Papadopoulos et al. |
| 2011/0027286 | A1 | 2/2011 | Thurston et al. |
| 2014/0243504 | A1 | 8/2014 | Davis et al. |
| 2015/0203580 | A1 | 7/2015 | Papadopoulos et al. |
| 2018/0112001 | A1 | 4/2018 | Haber et al. |

FOREIGN PATENT DOCUMENTS

| | | |
|---|---|---|
| WO | WO 2011/056983 | 5/2011 |
| WO | WO 2015/140212 A1 | 9/2015 |
| WO | WO2016149368 A1 | 9/2016 |
| WO | WO2018067331 A1 | 4/2018 |
| WO | WO2018114748 A1 | 6/2018 |
| WO | WO2018114754 A1 | 6/2018 |
| WO | WO2008119567 A2 | 10/2018 |

OTHER PUBLICATIONS

Yonezawa et al. (2015). Clin Cancer Res 21(14): 3113-3120.*
MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294: 151-162.*
Rudikoff et al. (1982). PNAS. 79:1979-1983.*
Altschul et al. (1990) "Basic Local Alignment Search Tool", J. Mol. Biol. 215:403-410.
Altschul et al. (1997) "Gapped BLAST and PSI-BLAST: a new generation of protein database search programs", Nucleic Acids Res. 25:3389-402.
Angal et al. (1993) "A Single Amino Acid Substitution Abolishes the Heterogeneity of Chimeric Mouse/Human (IgG4) Antibody", Molecular Immunology 30:105-108.

(Continued)

*Primary Examiner* — Christine J Saoud
*Assistant Examiner* — Jon M Lockard
(74) *Attorney, Agent, or Firm* — FisherBroyles, LLP; Cara L. Crowley-Weber; Aparna G. Patankar

(57) ABSTRACT

Provided herein are method of treating cancer using bispecific antigen-binding molecules that bind to Mucin 16 (MUC16) and CD3. According to certain embodiments, the antibodies useful herein bind human MUC16 with high affinity and bind CD3 to induce human T cell proliferation. According to certain embodiments, bispecific antigen-binding molecules comprising a first antigen-binding domain that specifically binds human CD3, and a second antigen-binding molecule that specifically binds human MUC16 are particularly useful herein. In certain embodiments, the bispecific antigen-binding molecules in combination with an anti-4-1BB agonist are capable of inhibiting the growth of tumors expressing MUC16, for example, ovarian tumors. The bispecific antigen-binding molecules in combination with an anti-4-1BB agonist are useful for the treatment of diseases and disorders in which an upregulated or induced targeted immune response is desired and/or therapeutically beneficial, for example, in the treatment of various cancers.

17 Claims, 6 Drawing Sheets

Specification includes a Sequence Listing.

(56) References Cited

OTHER PUBLICATIONS

Azad et al. (2016) "A fully human CXCR4 antibody demonstrates diagnostic utility and therapeutic efficacy in solid tumor xenografts", Oncotarget. 7(11):12344-12358.

Benedict et al. (1997) "Determination of the binding affinity of an anti-CD34 single-chain antibody using a novel, flow cytometry based assay", J Immunol Methods. 201(2):223-31.

Clynes et al. (1998) "Fc receptors are required in passive and active immunity to melanoma", Proc. Natl. Acad. Sci. (USA) 95:652-656.

Das et al. (2015) "Understanding the Unique Attributes of MUC16 (CA125): Potential Implications in Targeted Therapy", 75(22):4669-4674.

Deri et al. (2015) "p-SCN-Bn-HOPO: A Superior Bifunctional Chelator for 89Zr ImmunoPET", Bioconjugate Chem. 26 (12): 2579-2591.

Ehring (1999) "Hydrogen Exchange/Electrospray Ionization Mass Spectrometry Studies of Structural Features of Proteins and Protein/Protein Interactions", Analytical Biochemistry 267(2):252-259.

Engen and Smith (2001) "Peer reviewed: Investigating protein structure and dynamics by hydrogen exchange MS", Anal. Chem. 73:256A-265A.

Felder et al. (2014) "MUC16 (CA125): tumor biomarker to cancer therapy, a work in progress", Molecular Cancer, 13:129.

Geuijen et al. (2005) "Affinity ranking of antibodies using flow cytometry: Application in antibody phage display-based target discovery", J Immunol Methods. 302(1-2):68-77.

Gonnet et al. (1992) "Exhaustive Matching of the Entire Protein Sequence Database", Science 256: 1443-1445.

Haridas, D. et al., (2014) "MUC16: molecular analysis and its functional implications in benign and malignant conditions", FASEB J., 28:4183-4199.

Harlow and Lane (2014) Antibodies (Cold Spring Harbor Press, Cold Spring Harb., NY).

Junghans et al. (1990) "Anti-Tac-H, a Humanized Antibody to the Interleukin 2 Receptor with New Features for Immunotherapy in Malignant and Immune Disorders", Cancer Res. 50:1495-1502.

Klein et al. (2012) "Progress in overcoming the chain association issue in bispecific heterodimeric IgG antibodies", mAbs 4:6, 1-11.

Kufer et al. (2004) "A revival of bispecific antibodies", Trends Biotechnol. 22:238-244.

Langer (1990) "New Methods of Drug Delivery", Science 249:1527-1533.

Langer and Wise (1984) "Medical Applications of Controlled Release" Goodson in Medical Applications of Controlled Release, 2:115-138.

Mordenti et al. (1991) "Interspecies Scaling of Clearance and Volume of Distribution Data for Five Therapeutic Proteins", Pharmaceut. Res. 8:1351-1359.

Pandya et al. (2015) "Di-macrocyclic terephthalamide ligands as chelators for the PET radionuclide zirconium-89", Chem Commun (Camb) 51(12): 2301-2303.

Pearson (1994) "Using the FASTA Program to Search Protein and DNA Sequence Databases", Methods Mol. Biol. 24: 307-331.

Pearson (2000) "Flexible Sequence Similarity Searching with the FASTA3 Program Package", Methods Mol. Biol. 132:185-219.

Perk et al. (2010) "p-Isothiocyanatobenzyl-desferrioxamine: a new bifunctionalchelate for facile radiolabeling of monoclonal antibodies with zirconium-89 for immuno-PET imaging", Eur. J. Nucl. Med. Mol. Imaging 37:250-259.

Petrik et al. (2016) "In Vitro and In Vivo Comparison of Selected Ga-68 and Zr-89 Labelled Siderophores" Mol Imaging Biol 18(3):344-352.

Powell et al. (1998) "Compendium of excipients for parenteral formulations", PDA J Pharm Sci Technol 52:238-311.

Reineke (2004) "Antibody Epitope Mapping Using Arrays of Synthetic Peptides", Methods Mol Biol 248:443-463.

Schumacher et al. (2016) "Current Status: Site-Specific Antibody Drug Conugates", J.Clin.Immunol., 36:100-107.

Sefton (1987) "Implantable Pumps", Crit Rev Biomed Eng. 14(3):201-240.

Shield et al. (2002) "Lack of Fucose on Human IgG1 N-Linked Oligosaccharide Improves Binding to Human FcγRIII and Antibody-dependent Cellular Toxicity", JBC 277:26733.

Tavare et al. (2016) "An Effective Immuno-PET Imaging Method to Monitor CD8-Dependent Responses to Immunotherapy", Cancer Res. 76(1): 73-82.

Taylor et al.(1992) "A transgenic mouse that expresses a diversity of human sequence heavy and light chain Immunoglobulins", Nucl. Acids Res. 20:6287-6295.

Tomer (2000) "Characterization of a discontinuous epitope of the human immunodeficiency virus (HIV) core protein b24 by epitope excision and differential chemical modification followed by mass spectrometric peptide mapping analysis", Protein Science 9:487-496.

Tutt et al. (1991) "Trispecific F(ab')3 derivatives that use cooperative signaling via the TCR/CD3 complex and CD2 to activate and redirect resting cytotoxic T cells", J. Immunol. 147:60-69.

Van De Watering et al. (2014) "Zirconium-89 Labeled Antibodies: A New Tool for Molecular Imaging in Cancer Patients", BioMed Research International, vol. 2014, Article ID 203601.

Vosjan et al. (2010) "Conjugation and radiolabeling of monoclonal antibodies with zirconium-89 for PET imaging using the bifunctional chelate p-isothiocyanatobenzyl-desferrioxamine", Nature Protocols, 5(4): 739-743.

Vugts et al. (2017) "Comparison of the octadentate bifunctional chelator DFO*-pPhe-NCS and the clinically used hexadentate bifunctional chelator DFO-pPhe-NCS for 89Zr-immuno-PET", Eur. J. Nucl. Med. Mol. Imaging. 44:286-295 doi:10.1007/s00259-016-3499-x.

Wu et al. (1987) "Receptor-mediated in Vitro Gene Transformation by a Soluble DNA Carrier System", J. Biol. Chem. 262:4429-4432.

Zhai et al. (2015) "Novel Bifunctional Cyclic Chelator for 89Zr Labeling-Radiolabelingand Targeting Properties of RGD Conjugates", Mol. Pharmaceutics 12: 2142-2150.

Crawford, et al. (2019) "A Mucin 16 Bispecific T Cell-Engaging Antibody for the Treatment of Ovarian Cancer", Science Translational Medicine, 11(497):eaau7534.

Hamanishi, et al. (2016) "PD-1/PD-L1 Blockade in Cancer Treatment: Perspectives and Issues", Int. J. Clin. Oncol., 21:462-473.

International Search Report and Written Opinion for PCT/US2020/038669 mailed Sep. 29, 2020, 16 pages.

Skokos, et al. (2020) "A Class of Costimulatory CD28-Bispecific Antibodies that Enhance the Antitumor Activity of CD3-Bispecific Antibodies", Sci. Transl. Med., 12:aa7888, pp. 1-14.

Yeku, et al. (2019) "Bispecific Engager Immunotherapy Targeting the Retained Portion of MUC16 (MUC16ecto) is Efficacious Against Ovarian Cancer", Abstracts/Gynecologic Oncology, (154):57.

* cited by examiner

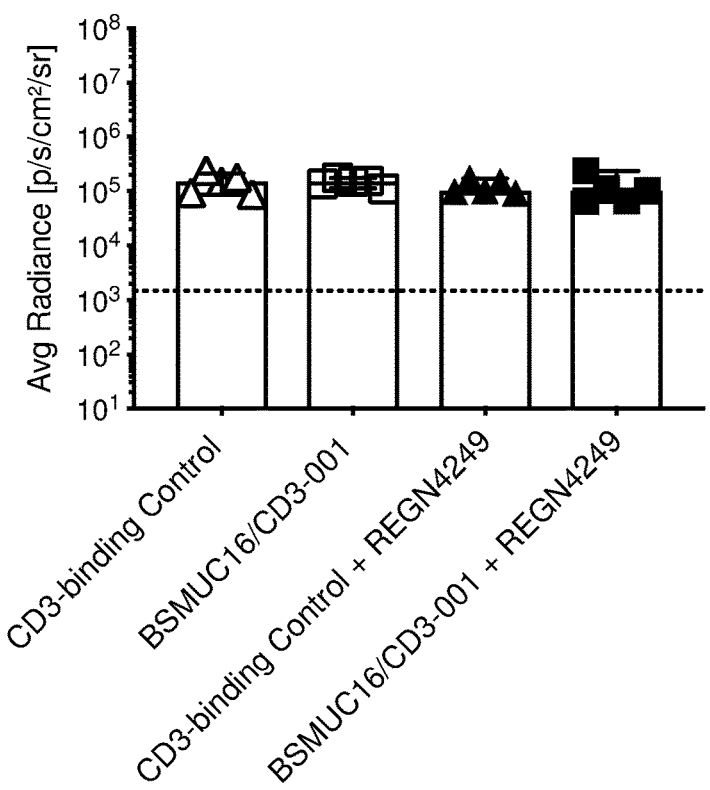
Figure 1: OVCAR-3 model study 1: Bioluminescence on Day 4 post tumor implantation

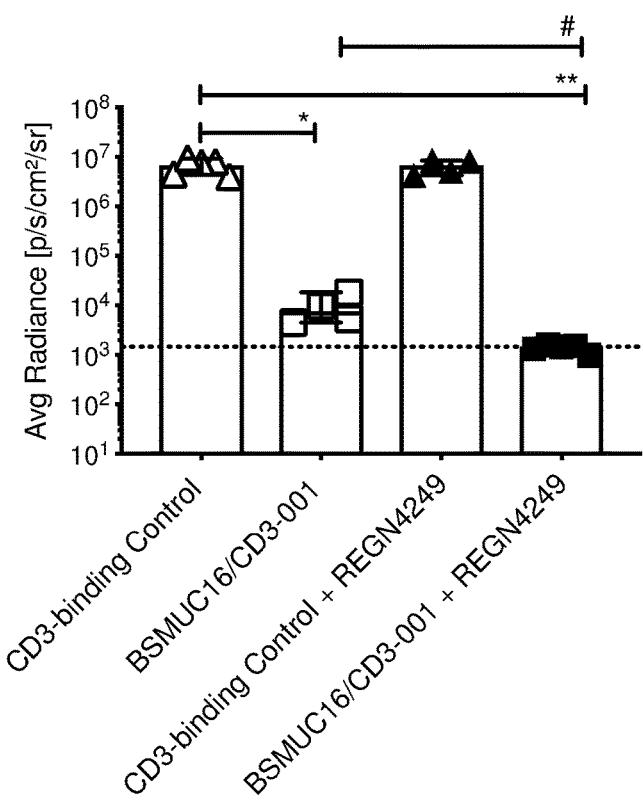
Figure 2: OVCAR-3 model study 1: Bioluminescence on Day 25 post tumor implantation

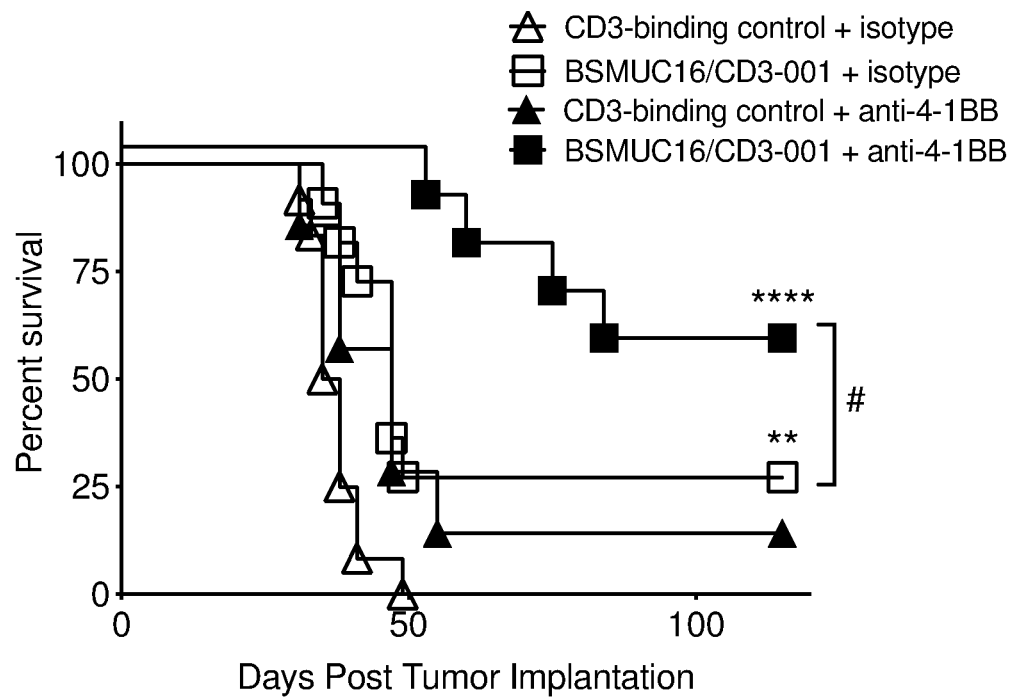
Figure 3: ID8-VEGF/huMUC16 model study 2: Survival curve

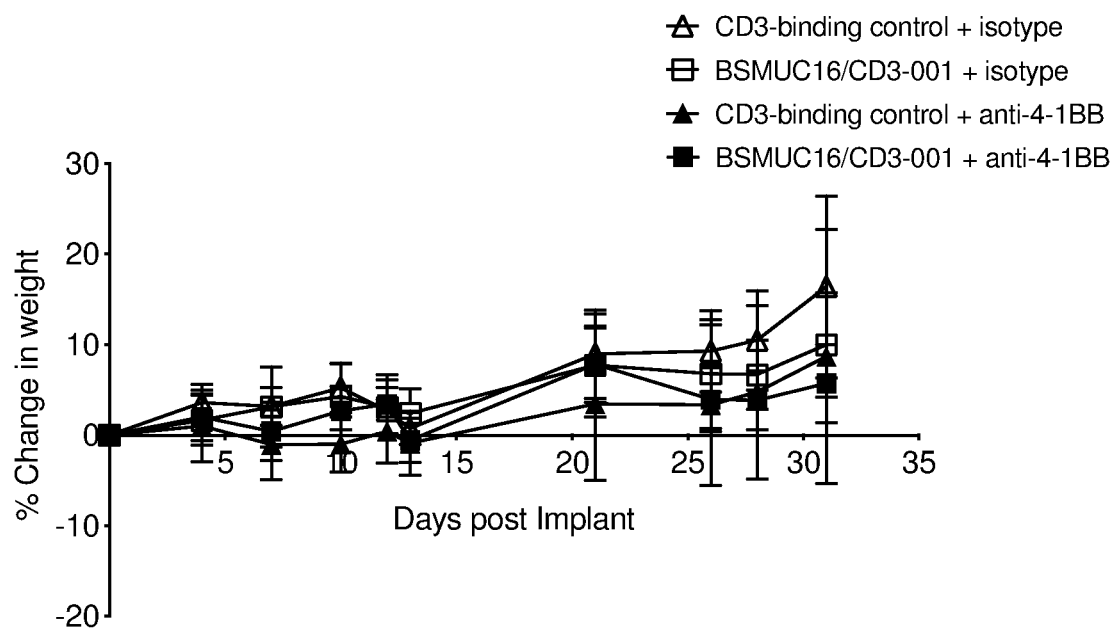
Figure 4: ID8-VEGF/huMUC16 model study 2: Weight change over time

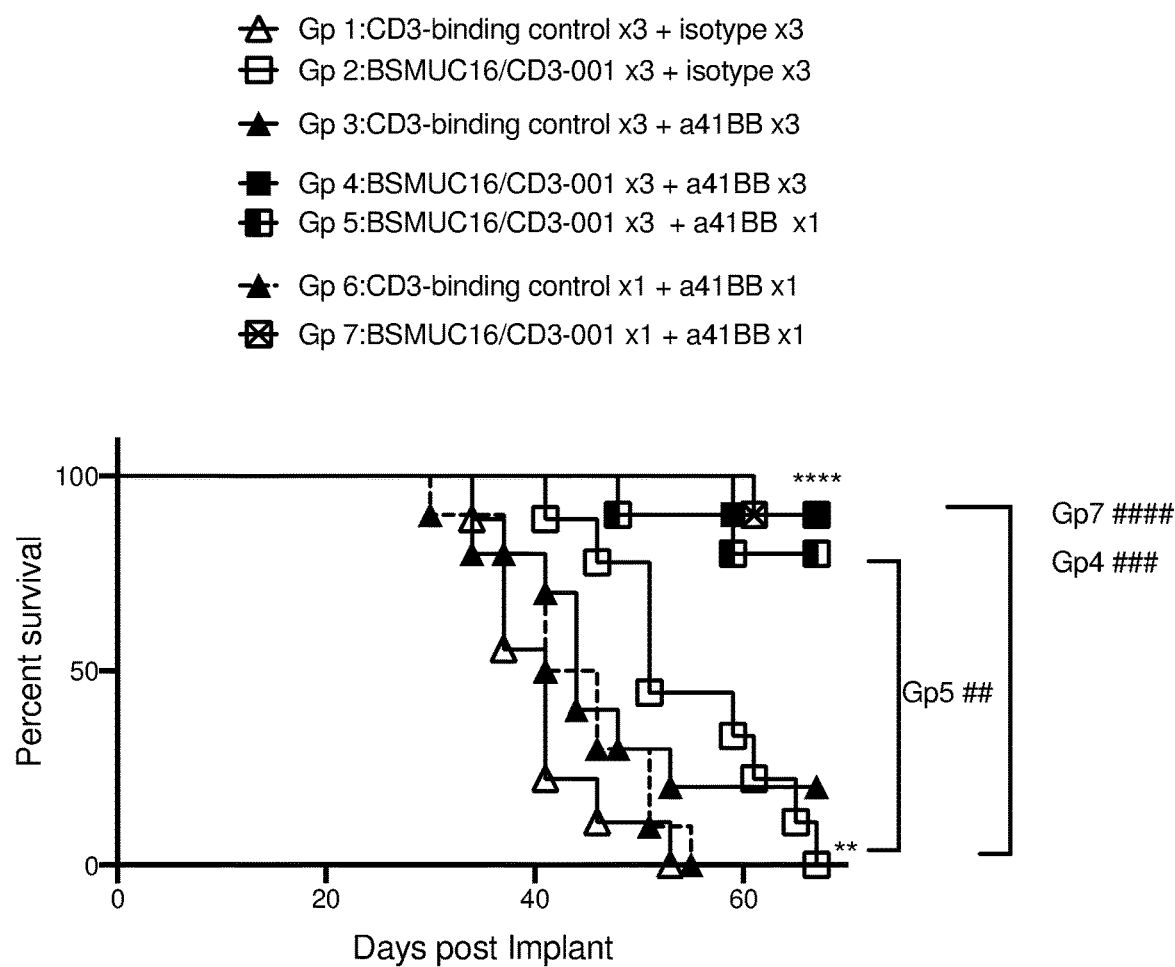
Figure 5: ID8-VEGF/huMUC16 model study 3: Survival curve

Figure 6: ID8-VEGF/huMUC16 model study 3: % change in weight
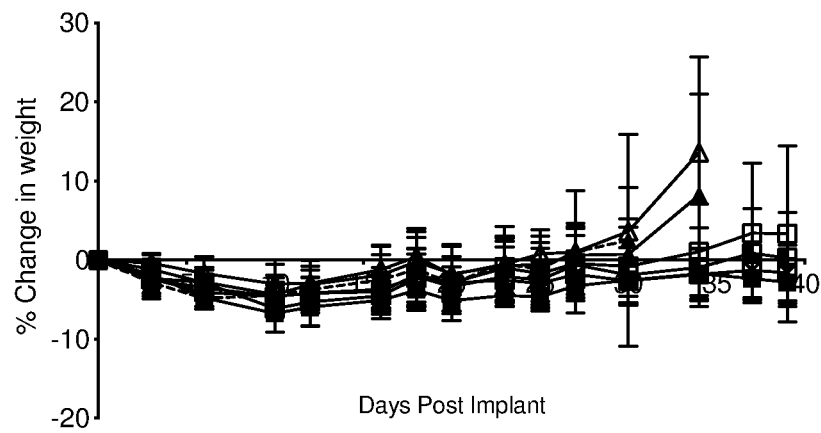

SEQUENCE LISTING

<160> NUMBER OF SEQ ID NOS: 6

<210> SEQ ID NO 1
<211> LENGTH: 117

```
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Ile
        35                  40                  45

Ser Tyr Ile Ser Gly Arg Gly Ser Thr Ile Phe Tyr Ala Asp Ser Val
    50                  55                  60

Lys Gly Arg Ile Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Val Lys Asp Arg Gly Gly Tyr Ser Pro Tyr Trp Gly Gln Gly Thr Leu
            100                 105                 110

Val Thr Val Ser Ser
        115

<210> SEQ ID NO 2
<211> LENGTH: 124
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 3
<211> LENGTH: 108
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
```

```
            20                  25                  30
Leu Asn Trp Tyr Gln Gln Lys Pro Gly Lys Ala Pro Lys Leu Leu Ile
            35                  40                  45

Tyr Thr Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 4
<211> LENGTH: 443
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Ile
        35                  40                  45

Ser Tyr Ile Ser Gly Arg Gly Ser Thr Ile Phe Tyr Ala Asp Ser Val
    50                  55                  60

Lys Gly Arg Ile Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Val Lys Asp Arg Gly Gly Tyr Ser Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
```

```
                275                 280                 285
Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 5
<211> LENGTH: 450
<212> TYPE: PRT
<213> ORGANISM: Artificial Sequence
<220> FEATURE:
<223> OTHER INFORMATION: Synthetic

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
```

```
            195                 200                 205
Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 6
<211> LENGTH: 215
<212> TYPE: PRT
<213> ORGANISM: Artificial Sequence
<220> FEATURE:
<223> OTHER INFORMATION: Synthetic

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg Thr Val Ala
```

-continued

```
            100                 105                 110
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215
```

USE OF BISPECIFIC ANTIGEN-BINDING MOLECULES THAT BIND MUC16 AND CD3 IN COMBINATION WITH 4-1BB CO-STIMULATION

CROSS-REFERENCE TO RELATED APPLICATIONS

This application claims the benefit under 35 U.S.C § 119(e) of U.S. Provisional Application Ser. No. 62/864,960, filed Jun. 21, 2019, which is herein specifically incorporated by reference in its entirety.

FIELD OF THE INVENTION

The present invention relates to bispecific antigen-binding molecules that bind Mucin 16 (MUC16) and CD3 in combination with 4-1BB co-stimulation, and methods of use thereof.

REFERENCE TO A SEQUENCE LISTING

An official copy of the sequence listing is submitted concurrently with the specification electronically via EFS-Web as an ASCII formatted sequence listing with a file name of 10604US01_SEQ_LIST_ST25, a creation date of Jun. 19, 2020, and a size of about 16,384 bytes. The sequence listing contained in this ASCII formatted document is part of the specification and is herein incorporated by reference in its entirety.

BACKGROUND

Mucin 16 (MUC16), also known as cancer antigen 125, carcinoma antigen 125, carbohydrate antigen 125, or CA-125, is a single transmembrane domain highly glycosylated integral membrane glycoprotein that is highly expressed in ovarian cancer. MUC16 consists of three major domains: an extracellular N-terminal domain, a large tandem repeat domain interspersed with sea urchin sperm, enterokinase, and agrin (SEA) domains, and a carboxyl terminal domain that comprises a segment of the transmembrane region and a short cytoplasmic tail. Proteolytic cleavage results in shedding of much of the extracellular portion of MUC16 into the bloodstream. MUC16 is overexpressed in cancers including ovarian cancer, breast cancer, pancreatic cancer, non-small-cell lung cancer, intrahepatic cholangiocarcinoma-mass forming type, adenocarcinoma of the uterine cervix, and adenocarcinoma of the gastric tract, and in diseases and conditions including inflammatory bowel disease, liver cirrhosis, cardiac failure, peritoneal infection, and abdominal surgery. (Haridas, D. et al., 2014, FASEB J., 28:4183-4199). Expression on cancer cells is shown to protect tumor cells from the immune system. (Felder, M. et al., 2014, Molecular Cancer, 13:129) Methods for treating ovarian cancer using antibodies to MUC16 have been investigated. Oregovomab and abgovomab are anti-MUC16 antibodies which have had limited success. (Felder, supra, Das, S. and Batra, S. K. 2015, Cancer Res. 75:4660-4674.)

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells. In addition, bispecific antibodies that are capable of binding CD3 and a target antigen have been proposed for therapeutic uses involving targeting T cell immune responses to tissues and cells expressing the target antigen.

In T-cell activation, co-stimulation via the TNF-receptor superfamily is key to survival, acquisition of effector functions, and memory differentiation. 4-1 BB (Tnfrsf9), also known as CD137, is a member of the TNF-receptor superfamily. Receptor expression is induced by lymphocyte activation following TCR-mediated priming, but its levels can be augmented by CD28 co-stimulation. Exposure to ligand or agonist monoclonal antibodies (mAb) on $CD8^+$ T cells costimulates 4-1 BB, contributing to the clonal expansion, survival, and development of T cells, induced proliferation in peripheral monocytes, activation of NF-kappaB, enhanced T cell apoptosis induced by TCR/CD3 triggered activation, and memory generation.

BRIEF SUMMARY

Provided herein are methods for treating a cancer in a subject. In some aspects, the methods comprise administering to the subject a pharmaceutical composition comprising an anti-MUC16 antibody or an anti-MUC16/anti-CD3 bispecific antigen-binding molecule and a pharmaceutically acceptable carrier or diluent, and further administering to the subject an anti-4-1BB agonist. In some aspects, the methods comprise administering to the subject a pharmaceutical composition comprising an anti-MUC16 antibody or an anti-MUC16/anti-CD3 bispecific antigen-binding molecule, an anti-4-1 BB agonist, and a pharmaceutically acceptable carrier or diluent. In some embodiments, the cancer is selected from the group consisting of ovarian cancer, breast cancer, pancreatic cancer, endometrial cancer, fallopian tube cancer, mesothelioma, non-small-cell lung cancer, intrahepatic cholangiocarcinoma-mass forming type, adenocarcinoma of the uterine cervix, and adenocarcinoma of the gastric tract. In some cases, the cancer is ovarian cancer. In some cases, the cancer is breast cancer.

Further provided herein are methods of treating cancer or inhibiting the growth of a tumor. In some aspects, the methods comprise administering to a subject in need thereof a therapeutically effective amount of each of (a) an anti-MUC16 antibody or antigen-binding fragment thereof or an anti-CD3/anti-MUC16 bispecific antigen-binding molecule; and (b) an anti-4-1BB agonist.

Also provided herein are therapeutic methods for targeting/killing tumor cells expressing MUC16. In some aspects, the therapeutic methods comprise administering a therapeutically effective amount of an anti-MUC16 antibody or an anti-CD3/anti-MUC16 bispecific antigen-binding molecule and a therapeutically effective amount of an anti-4-1BB agonist to a subject in need thereof. In some aspects, the anti-MUC16 antibody or anti-CD3/anti-MUC16 bispecific antigen-binding molecule and the anti-4-1 BB agonist are formulated separately. In some aspects, the anti-MUC16 antibody or anti-CD3/anti-MUC16 bispecific antigen-binding molecule and the anti-4-1 BB agonist are formulated in the same pharmaceutical composition.

Also provided herein is the use of an anti-MUC16 antibody or an anti-CD3/anti-MUC16 bispecific antigen-binding molecule with an anti-4-1BB agonist in the manufacture of a medicament for the treatment of a disease or disorder related to or caused by MUC16-expressing cells.

Administration of an anti-MUC16 antibody or antigen-binding fragment thereof, or an anti-MUC16/anti-CD3 bispecific antigen-binding molecule, in the presence of an anti-4-1 BB agonist can decrease tumor volume relative to tumor volume in a subject administered the anti-MUC16 antibody or anti-CD3/anti-MUC16 bispecific antigen-binding molecule in the absence of an anti-4-1BB agonist.

Administration of an anti-MUC16 antibody or antigen-binding fragment thereof, or an anti-MUC16/anti-CD3 bispecific antigen-binding molecule, in the presence of an anti-4-1 BB agonist can increase tumor free survival time in the subject relative to tumor free survival time in a subject administered the anti-MUC16 antibody or anti-CD3/anti-MUC16 bispecific antigen-binding molecule in the absence of an anti-4-1BB agonist. In some aspects, the increase in tumor free survival time occurs without weight loss in the subject.

Administration of an anti-MUC16 antibody or antigen-binding fragment thereof, or an anti-MUC16/anti-CD3 bispecific antigen-binding molecule in the presence of an anti-4-1 BB agonist can elicit a memory response in the subject treated with the anti-MUC16 antibody or anti-CD3/anti-MUC16 bispecific antigen-binding molecule in the presence of an anti-4-1BB agonist upon subsequent exposure to tumor cells.

An anti-4-1BB agonist can be a small molecule or biologic agonist of 4-1 BB, and in some aspects is an antibody. Exemplary anti-4-1 BB agonists include commercially available antibodies, for example anti-mouse 4-1 BB agonists, and therapeutic antibodies such as urelumab and utomilumab.

Useful according to the methods provided herein are anti-MUC16 antibodies or antigen-binding fragments thereof and bispecific antibodies and antigen-binding fragments thereof that bind human MUC16 and human CD3. The bispecific antibodies are useful, inter alia, for targeting T cells expressing CD3, and for stimulating T cell activation, e.g., under circumstances where T cell-mediated killing of cells expressing MUC16 is beneficial or desirable. For example, the bispecific antibodies can direct CD3-mediated T cell activation to specific MUC16-expressing cells, such as ovarian tumor cells.

Anti-MUC16 antibodies or antigen-binding fragments thereof that bind MUC16 are useful in combination with an anti-4-1BB agonist for treating diseases and disorders related to or caused by MUC16-expressing tumors, and particularly, tumors that are larger and/or more difficult to treat. Exemplary anti-MUC16 antibodies and antigen-binding fragments thereof are described in detail in U.S. 2018/0112001. In some aspects, the anti-MUC16 antibody comprises an HCVR of SEQ ID NO: 18 and an LCVR of SEQ ID NO: 26 referred to in U.S. 2018/0112001. In some aspects, the anti-MUC16 antibody is the H1H8767P antibody referred to in U.S. 2018/0112001.

In addition, exemplary bispecific antigen-binding molecules that bind both MUC16 and CD3 are described in U.S. Publication No. 2018/0112001, incorporated by reference herein.

Bispecific antigen-binding molecules (e.g., antibodies) that bind MUC16 and CD3 are also referred to herein as "anti-MUC16/anti-CD3 bispecific molecules," "anti-CD3/anti-MUC16 bispecific molecules," "MUC16×CD3 bsAbs", or simply "MUC16×CD3". The anti-MUC16 portion of the anti-MUC16/anti-CD3 bispecific molecule is useful for targeting cells (e.g., tumor cells) that express MUC16 (e.g., ovarian tumors), and the anti-CD3 portion of the bispecific molecule is useful for activating T-cells. The simultaneous binding of MUC16 on a tumor cell and CD3 on a T-cell facilitates directed killing (cell lysis) of the targeted tumor cell by the activated T-cell. The anti-MUC16/anti-CD3 bispecific molecules are therefore useful, inter alia, for treating diseases and disorders related to or caused by MUC16-expressing tumors (e.g., ovarian tumors). The anti-MUC16/anti-CD3 bispecific molecules are also useful in combination with an anti-4-1 BB agonist for treating diseases and disorders related to or caused by MUC16-expressing tumors, and for effecting a memory response and/or epitope spreading. In some aspects, the anti-MUC16/anti-CD3 bispecific antigen-binding molecules in combination with an anti-4-1BB agonist are useful effecting an anti-tumor response independent of the presence of or response to MUC16 antigen, particularly in suppressing a secondary tumor challenge.

The bispecific antigen-binding molecules comprise a first antigen-binding domain that specifically binds human CD3, and a second antigen-binding domain that specifically binds MUC16.

Exemplary bispecific antibodies useful according to the methods provided herein are anti-CD3/anti-MUC16 bispecific molecules, wherein the first antigen-binding domain that specifically binds CD3 comprises any of the heavy chain variable region (HCVR) amino acid sequences, any of the light chain variable region (LCVR) amino acid sequences, any of the HCVR/LCVR amino acid sequence pairs, any of the heavy chain CDR1-CDR2-CDR3 amino acid sequences, or any of the light chain CDR1-CDR2-CDR3 amino acid sequences as set forth in U.S. Publication No. 2018/0112001.

Useful according to the methods provided herein are anti-CD3/anti-MUC16 bispecific antigen-binding molecules, wherein the first antigen-binding domain that specifically binds CD3 comprises any of the HCVR amino acid sequences and/or any of the LCVR amino acid sequences, or a substantially similar sequence thereof having at least 90%, at least 95%, at least 98% or at least 99% sequence identity, as set forth in Tables 16, 18, 19, 22, and 24 of U.S. Publication No. 2018/0112001. In some aspects, the first antigen-binding domain that specifically binds CD3 comprises a HCVR-1 amino acid sequence of SEQ ID NO: 2. In some aspects, the first antigen-binding domain that specifically binds CD3 comprises a full length heavy chain amino acid sequence of SEQ ID NO: 5.

Useful according to the methods provided herein are anti-CD3/anti-MUC16 bispecific molecules, wherein the second antigen-binding domain that specifically binds MUC16 comprises any of the HCVR amino acid sequences and/or any of the LCVR amino acid sequences, or a substantially similar sequence thereof having at least 90%, at least 95%, at least 98%, or at least 99% sequence identity, as set forth in Table 1 of U.S. Publication No. 2018/0112001. In some aspects, the second antigen-binding domain that specifically binds MUC16 comprises a HCVR-2 amino acid sequence of SEQ ID NO: 1. In some aspects, the second antigen-binding domain that specifically binds MUC16 comprises a full length heavy chain amino acid sequence of SEQ ID NO: 4.

Useful according to the methods provided herein are anti-CD3/anti-MUC16 bispecific molecules comprising any of the sequences, or substantially similar sequences thereof having at least 90%, at least 95%, at least 98%, or at least 99% sequence identity, as set forth in Table 4 of U.S. Publication No. 2018/0112001.

Useful according to the methods provided herein are anti-CD3/anti-MUC16 bispecific molecules, wherein the first antigen-binding domain that specifically binds CD3 comprises a HCVR-1 amino acid sequence of SEQ ID NO: 2 and wherein the second antigen-binding domain that specifically binds MUC16 comprises a HCVR-2 amino acid sequence of SEQ ID NO: 1. In some aspects, the anti-CD3/anti-MUC16 bispecific molecule comprises a common LCVR amino acid sequence of SEQ ID NO: 3.

Useful according to the methods provided herein are anti-CD3/anti-MUC16 bispecific antigen-binding molecules, wherein the first antigen-binding domain that specifically binds CD3 comprises a full length heavy chain amino acid sequence of SEQ ID NO: 5 and wherein the second antigen-binding domain that specifically binds MUC16 comprises a full length heavy chain amino acid sequence of SEQ ID NO: 4. In some aspects, the anti-CD3/anti-MUC16 bispecific molecule comprises a full length light chain amino acid sequence of SEQ ID NO: 6.

In one aspect, provided herein is a pharmaceutical composition comprising an anti-MUC16 antigen-binding molecule or anti-MUC16/anti-CD3 bispecific antigen-binding molecule and a pharmaceutically acceptable carrier or diluent. In some aspects, the pharmaceutical composition further comprises an anti-4-1BB agonist.

Useful according to the methods of the present disclosure are anti-MUC16 antibodies and antigen-binding fragments thereof and anti-CD3/anti-MUC16 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277: 26733). In other applications, modification of galactosylation can be made in order to modify complement dependent cytotoxicity (CDC).

In one aspect, the disclosure provides a pharmaceutical composition comprising an anti-MUC16 antibody or antigen binding fragment thereof or an anti-CD3/anti-MUC16 bispecific antigen-binding molecule as disclosed herein, an anti-4-1BB agonist, and a pharmaceutically acceptable carrier. In a related aspect, the disclosure features a composition which is a combination of an anti-MUC16 antibody or antigen binding fragment thereof or an anti-CD3/anti-MUC16 bispecific antigen-binding molecule, an anti-4-1BB agonist, and a third therapeutic agent. In one embodiment, the third therapeutic agent is any agent that is advantageously combined with an anti-MUC16 antibody or antigen binding fragment thereof or an anti-CD3/anti-MUC16 bispecific antigen-binding molecule. Exemplary agents that may be advantageously combined with an anti-CD3/anti-MUC16 bispecific antigen-binding molecule are discussed in detail elsewhere herein.

In another aspect, provided herein are radiolabeled anti-MUC16 antibody conjugates or anti-CD3/anti-MUC16 bispecific antigen-binding molecule conjugates for use in immuno-PET imaging. The conjugate comprises an anti-MUC16 antibody or an anti-CD3/anti-MUC16 bispecific antigen-binding molecule, a chelating moiety, and a positron emitter.

Provided herein are processes for synthesizing said conjugates and synthetic intermediates useful for the same.

Provided herein are methods of imaging a tissue that expresses MUC16, the methods comprising administering a radiolabeled anti-MUC16 antibody conjugate or anti-CD3/anti-MUC16 bispecific antigen-binding molecule conjugate described herein to the tissue; and visualizing the MUC16 expression by positron emission tomography (PET) imaging.

Provided herein are methods of imaging a tissue comprising MUC16-expressing cells, the methods comprising administering a radiolabeled anti-MUC16 antibody conjugate or anti-CD3/anti-MUC16 bispecific antigen-binding molecule conjugate described herein to the tissue, and visualizing the MUC16 expression by PET imaging.

Provided herein are methods for detecting MUC16 in a tissue, the methods comprising administering a radiolabeled anti-MUC16 antibody conjugate or anti-CD3/anti-MUC16 bispecific antigen-binding molecule conjugate described herein to the tissue; and visualizing the MUC16 expression by PET imaging. In one embodiment, the tissue is present in a human subject. In certain embodiments, the subject is a non-human mammal. In certain embodiments, the subject has a disease or disorder such as cancer, an inflammatory disease, or an infection.

Provided herein are methods for detecting MUC16 in a tissue, the methods comprising contacting the tissue with an anti-MUC16 antibody conjugate or anti-CD3/anti-MUC16 bispecific antigen-binding molecule conjugated to a fluorescent molecule described herein; and visualizing the MUC16 expression by fluorescence imaging.

Provided herein are methods for identifying a subject to be suitable for anti-tumor therapy, the methods comprising selecting a subject with a solid tumor, administering a radiolabeled anti-MUC16 antibody conjugate or anti-CD3/anti-MUC16 bispecific antigen-binding molecule conjugate described herein, and visualizing the administered radiolabeled antibody conjugate in the tumor by PET imaging wherein presence of the radiolabeled antibody conjugate in the tumor identifies the subject as suitable for anti-tumor therapy.

Provided herein are methods of treating a tumor, the methods comprising selecting a subject with a tumor; determining that the tumor is MUC16 positive; and administering an anti-tumor therapy to the subject in need thereof. In certain embodiments, the anti-tumor therapy comprises an inhibitor of the PD-1/PD-L1 signaling axis (e.g., an anti-PD-1 antibody or an anti-PD-L1 antibody), an example of a checkpoint inhibitor therapy. In certain embodiments, the subject is administered a radiolabeled anti-MUC16 antibody conjugate or anti-CD3/anti-MUC16 bispecific antigen-binding molecule conjugate described herein, and localization of the radiolabeled antibody conjugate is imaged via positron emission tomography (PET) imaging to determine if the tumor is MUC16 positive. In certain embodiments, the subject is further administered a radiolabeled anti-PD-1 antibody conjugate, and localization of the radiolabeled antibody conjugate is imaged via positron emission tomography (PET) imaging to determine if the tumor is PD-1-positive.

Provided herein are methods for monitoring the efficacy of an anti-tumor therapy in a subject, wherein the methods comprise selecting a subject with a solid tumor wherein the subject is being treated with an anti-tumor therapy; administering a radiolabeled anti-MUC16 antibody conjugate or anti-CD3/anti-MUC16 bispecific antigen-binding molecule conjugate described herein to the subject; imaging the localization of the administered radiolabeled conjugate in the tumor by PET imaging; and determining tumor growth, wherein a decrease from the baseline in uptake of the conjugate or radiolabeled signal indicates efficacy of the anti-tumor therapy.

In certain embodiments, the anti-tumor therapy comprises a PD-1 inhibitor (e.g., REGN2810, BGB-A317, nivolumab, pidilizumab, and pembrolizumab), a PD-L1 inhibitor (e.g., atezolizumab, avelumab, durvalumab, MDX-1105, and REGN3504, as well as those disclosed in Patent Publication No. US 2015-0203580), CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to LAGS, CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGES), carcinoembryonic antigen (CEA), vimentin, tumor-M2-PK, prostate-specific antigen (PSA), prostate-specific membrane antigen (PSMA), also known as folate hydrolase 1 (FOLH1), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA× CD3 bispecific antibody), a cytotoxin, a poly ADP-ribose polymerase (PARP) inhibitor, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, and an antibody-drug conjugate (ADC) (e.g., anti-CD19-DM4 ADC, and anti-DS6-DM4 ADC).

Other embodiments will become apparent from a review of the ensuing detailed description.

BRIEF DESCRIPTION OF THE DRAWINGS

FIG. 1 shows the results of the OVCAR-3 model study 1 (Avg Radiance [p/s/cm$^2$/sr] at Day 4). All groups had similar tumor burden as assessed by BLI before dosing started. Data shown is tumor burden as assessed by BLI on Day 4 post tumor implantation. Statistical significance was determined using unpaired nonparametric Mann-Whitney t-tests. There was no significant difference in tumor burden between groups before dosing started.

FIG. 2 shows the results of the OVCAR-3 model study 1 (Avg Radiance [p/s/cm 2$^2$/sr] at Day 25). BSMUC16/CD3-001 significantly reduces tumor burden at 12.5 ug and addition of anti-4-1BB enhances the anti-tumor efficacy over that of BSMUC16/CD3-001 alone. NSG mice engrafted with human T cells were implanted with human OVCAR-3/Luc cells. Mice were treated on days 5 and 8 days post tumor implantation with BSMUC16/CD3-001 (12.5 ug IV) or a CD3-binding control (12.5 ug IV) alone or in combination with anti-4-1BB agonist (100 ug IV). Data shown is tumor burden as assessed by BLI on Day 25 post tumor implantation. Statistical significance was determined using unpaired nonparametric Mann-Whitney t-tests. Groups were compared to the CD3-binding control (* p=0.0159 for BSMUC16/CD3-001, ** p<0.0079 for BSMUC16/CD3-001 and anti-4-1 BB combination). BSMUC16/CD3-001 and anti-4-1BB combination was also compared to BSMUC16/CD3-001 alone (#p=0.0159).

FIG. 3 shows the results of the ID8-VEGF/huMUC16 mouse model treated with BSMUC16/CD3-001+anti-4-1 BB combination. BSMUC16/CD3-001 treatment significantly increases median survival time in the ID8-VEGF/huMUC16 ascites model and addition of 4-1BB co-stimulation allows survival of several mice. Mice expressing human CD3 in place of mouse CD3 and a chimeric MUC16 molecule were implanted with the murine ovarian tumor line expressing a portion of human MUC16. Mice were administered either BSMUC16/CD3-001 (1 mg/kg IV) or CD3-binding control (1 mg/kg IV) with isotype control on days 3, 6 and 10 post implantation or with anti-4-1BB (clone LOB12.3, 2.5 mg/kg IV) on day 3 post implantation followed by two additional doses of BSMUC16/CD3-001 (1 mg/kg IV) on days 6 and 10. Mice were sacrificed when they had a with weight-gain of more than 30% due to ascites-induced abdominal distension. Statistical significance was determined using the Gehan-Breslow-Wilcoxon method. For statistical analysis, groups were compared to the CD3-binding control (p=0.0026 for BSMUC16/CD3-001, ** p<0.0001 for BSMUC16/CD3-001 with anti-4-1BB). In addition, to determine whether addition of anti-4-1BB had any beneficial outcome over BSMUC16/CD3-001 alone, anti-4-1BB was compared to BSMUC16/CD3-001 alone (#p=0.0168). BSMUC16/CD3-001 increased the median survival time over the CD3-binding control group as well as the % of mice surviving (from 0 to 27%). The median survival time for the BSMUC16/CD3-001+anti-4-1BB combination group could not be defined since more than 50% of mice survived. The total survival of the combination treated group was 55%.

FIG. 4 depicts weight change over time. The treatment with BSMUC16/CD3-001+anti-4-1BB combination as shown in FIG. 3 did not elicit any significant weight loss during the dosing period, which was used as a read-out for toxicity.

FIG. 5 provides data from a second study of the ID8-VEGF/huMUC16 mouse model treated with 3 different dosing regimens of the BSMUC16/CD3-001+anti-4-1 BB combination: A) Combination of either BSMUC16/CD3-001 (1 mg/kg i.v.) or CD3-binding control (1 mg/kg i.v.) with either isotype control (2.5 mg/kg IV) or anti-4-1 BB (2.5 mg/kg i.v.) on days 3, 7, and 10 post-implantation; B) One dose of combination of BSMUC16/CD3-001(1 mg/kg i.v.) plus anti-4-1 BB (2.5 mg/kg i.v.) on day 3 post implantation followed by doses of BSMUC16/CD3-001(1 mg/kg i.v.) on days 7 and 10 post-implantation; C) One dose of combination of BSMUC16/CD3-001 (1 mg/kg i.v.) or CD3-binding control (1 mg/kg i.v.) plus anti-4-1BB (2.5 mg/kg i.v.) day 3 post implantation with no further treatments. Data shown is median survival. Mice were sacrificed when they had weight-gain of more than 30% due to ascites-induced abdominal distension. Statistical significance was determined using the Gehan-Breslow-Wilcoxon method. For statistical analysis, groups were compared to the CD3-binding control (p=0.002 for BSMUC16/CD3-001, ** p<0.0001 for all three groups consisting of BSMUC16/CD3-001 and anti-4-1 BB in combination). In addition, to determine whether combination with anti-4-1BB had any beneficial outcome over BSMUC16/CD3-001 alone, all groups were compared to this group (#p=0.011 for Gp4 (3 doses of CD3 bispecific+3 doses of anti-4-1 BB), #p=0.027 for Gp5 (3 doses of CD3 bispecific+only 1 dose of anti-4-1 BB), #p=0.011 for Gp7 (one dose of CD3 bispecific+anti-4-1BB)).

FIG. 6 depicts weight change over time. The treatment with the different dosing regimens of the BSMUC16/CD3-001+anti-4-1BB combination as shown in FIG. 5 did not elicit any significant weight loss during the dosing period, which was used as a read-out for toxicity.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, the preferred methods and materials are now described. All patents, applications and non-patent publications mentioned in this specification are incorporated herein by reference in their entireties.

As shown in the Examples, MUC16×CD3 bispecific antibodies were efficacious in treating ovarian tumors in several mouse models. However, the inventors sought to enhance and prolong MUC16×CD3 induced T cell activity by providing a costimulatory signal using an anti-4-1BB agonist. The 4-1BB signaling pathway can enhance the magnitude and duration of T cell responses by promoting T cell survival, reversing T cell anergy, and subsequently generating memory T cells to promote potent anti-tumor activity and epitope broadening.

As shown herein, combining a MUC16×CD3 bispecific antibody with anti-4-1 BB co-stimulation resulted in striking anti-tumor efficacy in ovarian tumors. Anti-tumor effects were seen in the absence of weight loss. This combination was also shown to induce tumor-specific T cell memory and initiate epitope broadening. This combination was also shown to effect an anti-tumor response independent of the presence of or response to MUC16 antigen, particularly in suppressing a secondary tumor challenge.

The ability of anti-MUC16 antibodies and MUC16×CD3 bispecific antibodies in combination with 4-1 BB co-stimulation enhances the magnitude and duration of the T cell response leading to remarkable anti-tumor efficacy as demonstrated herein. Combining anti-MUC16 antibodies or MUC16×CD3-bispecific antibodies with 4-1 BB co-stimulation is useful in methods of treating tumors to achieve better overall survival.

Therapeutic Uses of the Antigen-Binding Molecules

The present disclosure includes methods comprising administering to a subject in need thereof an anti-MUC16 antibody or antigen-binding fragment thereof or a bispecific antigen-binding molecule that specifically binds CD3 and MUC16, with an anti-4-1BB agonist. A therapeutic composition useful according to the methods herein can comprise an anti-MUC16 antibody or a MUC16×CD3-bispecific antigen-binding molecule and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in MUC16 activity or a depletion of MUC16+ cells (e.g., ovarian cancer cells).

The antibodies and bispecific antigen-binding molecules disclosed herein (and therapeutic compositions comprising the same) are useful, inter alia, in combination with an anti-4-1 BB agonist for treating any disease or disorder in which stimulation, activation and/or targeting of an immune response would be beneficial. In particular, the anti-MUC16 antibodies and anti-CD3/anti-MUC16 bispecific antigen-binding molecules combined with the anti-4-1BB agonist may be used for the treatment, prevention and/or amelioration of any disease or disorder associated with or mediated by MUC16 expression or activity or the proliferation of MUC16+ cells. The mechanism of action by which the therapeutic methods disclosed herein are achieved include killing of the cells expressing MUC16 in the presence of effector cells, for example, by CDC, apoptosis, ADCC, phagocytosis, or by a combination of two or more of these mechanisms. Cells expressing MUC16 which can be inhibited or killed using the antibodies or bispecific antigen-binding molecules include, for example, ovarian tumor cells. Further therapeutic effect is achieved by 4-1BB co-stimulation, including contributing to the clonal expansion, survival, and development of T cells, induced proliferation in peripheral monocytes, activation of NF-kappaB, enhanced T cell apoptosis induced by TCR/CD3 triggered activation, and memory generation.

The antigen-binding molecules, including anti-MUC16 antibodies and anti-MUC16/anti-CD3 bispecific antibodies, in combination with an anti-4-1 BB agonist may be used to treat, e.g., primary and/or metastatic tumors such as ovarian cancer, breast cancer, pancreatic cancer, endometrial cancer, fallopian tube cancer, mesothelioma, non-small-cell lung cancer, intrahepatic cholangiocarcinoma-mass forming type, adenocarcinoma of the uterine cervix, and adenocarcinoma of the gastric tract, and diseases and conditions including inflammatory bowel disease, liver cirrhosis, cardiac failure, peritoneal infection, and abdominal surgery. In certain embodiments, the antibodies or bispecific antigen-binding molecules are used to treat one or more of the following cancers: ovarian cancer, breast cancer, pancreatic cancer, endometrial cancer, fallopian tube cancer, mesothelioma, non-small-cell lung cancer, intrahepatic cholangiocarcinoma-mass forming type, adenocarcinoma of the uterine cervix, and adenocarcinoma of the gastric tract. According to certain embodiments of the present disclosure, the anti-MUC16 antibodies or anti-MUC16/anti-CD3 bispecific antibodies in combination with an anti-4-1 BB agonist are useful for treating a patient afflicted with ovarian cancer or breast cancer. According to other related embodiments disclosed herein, methods are provided comprising administering an anti-CD3/anti-MUC16 bispecific antigen-binding molecule in combination with an anti-4-1BB agonist to a patient who is afflicted with ovarian or breast cancer.

The present disclosure also includes methods for initiating a memory response and/or epitope broadening. The present disclosure also includes methods for effecting an anti-tumor response independent of the presence of or response to MUC16 antigen, for example, in suppressing a secondary tumor challenge.

The present disclosure also includes methods for treating residual cancer in a subject. As used herein, the term "residual cancer" means the existence or persistence of one or more cancerous cells in a subject following treatment with an anti-cancer therapy.

According to certain aspects, the present disclosure provides methods for treating a disease or disorder associated with MUC16 expression (e.g., ovarian cancer) comprising administering one or more of the bispecific antigen-binding molecules described elsewhere in combination with an anti-4-1BB agonist to a subject after the subject has been determined to have ovarian cancer. For example, the present disclosure includes methods for treating ovarian cancer comprising administering an anti-CD3/anti-MUC16 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received hormone therapy (e.g., anti-androgen therapy).

Definitions

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments useful herein may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

The expression "MUC16," as used herein, refers to Mucin 16, also known as cancer antigen 125 (CA125). MUC16 is a large membrane associated mucin having a single transmembrane domain. This cell surface glycoprotein is highly expressed in ovarian cancer and plays a role in promoting cancer cell growth. As used herein, "an antibody that binds MUC16" or an "anti-MUC16 antibody" includes antibodies and antigen-binding fragments thereof that specifically recognize MUC16.

The expression "4-1 BB" as used herein, also known as CD137, refers to an activation-induced costimulatory molecule. 4-1BB is an important regulator of immune responses and is a member of the TNF-receptor superfamily. The expression "anti-4-1BB agonist" is any ligand that binds 4-1 BB and activates the receptor. Exemplary anti-4-1BB agonists include urelumab (BMS-663513), and utomilumab (PF-05082566), and commercially available anti-mouse 4-1 BB antibodies. In addition, the term "4-1 BB agonist" refers to any molecule that partially or fully promotes, induces, increases, and/or activates a biological activity of 4-1 BB. Suitable agonist molecules specifically include agonist antibodies or antibody fragments, including bispecific antibodies, e.g. a bispecific antibody comprising one arm that binds 4-1BB on an immune cell and the other arm binds to, for example, an antigen on a tumor target. The term also includes fragments or amino acid sequence variants of native polypeptides, peptides, antisense oligonucleotides, small organic molecules, etc. In some embodiments, activation in the presence of the agonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than the signal measured with a negative control under comparable conditions. Efficacy of an agonist can also be determined using functional assays, such as the ability of an agonist to activate or promote the function of the polypeptide. For example, a functional assay may comprise contacting a polypeptide with a candidate agonist molecule and measuring a detectable change in one or more biological activities normally associated with the polypeptide. The potency of an agonist is usually defined by its $EC_{50}$ value (concentration required to activate 50% of the agonist response). The lower the $EC_{50}$ value the greater the potency of the agonist and the lower the concentration that is required to activate the maximum biological response. A 4-1 BB agonist may also include a molecule containing the 4-1 BB-Ligand or a fragment of the 4-1BB-Ligand, e.g., a bispecific molecule comprising one arm that contains 4-1 BBL or fragment thereof and the other arm binds to, for example, an antigen on a tumor. These fragments may include an Fc region.

The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., MUC16 or CD3). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments disclosed herein, the FRs of the anti-MUC16 antibody or anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody useful herein include: (i) $V_H$-$C_H1$; $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody useful herein may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody useful herein using routine techniques available in the art.

The antibodies useful herein may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody disclosed herein in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the anti-MUC16 antibodies or anti-MUC16/anti-CD3 bispecific antibodies useful herein are human antibodies. The term "human antibody", as used herein, is intended to include antibodies having variable and constant regions derived from human germline immunoglobulin sequences. The human antibodies may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies useful according to the methods disclosed herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form.

The antibodies useful herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-MUC16 antibodies and anti-MUC16/anti-CD3 antibodies useful according to the methods disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies useful herein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

Useful according to the methods provided herein are anti-MUC16 antibodies and anti-MUC16/anti-CD3 antibodies comprising variants of any of the HCVR, LCVR, and/or CDR amino acid sequences disclosed herein having one or more conservative substitutions. For example, the present disclosure includes anti-MUC16 antibodies and anti-MUC16/anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the heavy chain or light chain amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence disclosed herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Sequence Variants

The antibodies and bispecific antibodies useful herein comprise one or more amino acid substitutions, insertions and/or deletions in the framework and/or CDR regions of the heavy chain variable domains as compared to the corresponding germline sequences from which the antibodies were derived.

Also useful herein are antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), and having weak or no detectable antigen binding.

Furthermore, the antibodies useful herein may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired properties such as, improved binding specificity, weak or reduced binding affinity, improved or enhanced pharmacokinetic properties, reduced immunogenicity, etc. Antibodies and antigen-binding fragments obtained in this general manner given the guidance of the present disclosure are encompassed within the present invention.

Useful according to the present disclosure are antibodies and bispecific antibodies comprising variants of any of the heavy chain or light chain amino acid sequences provided herein having one or more conservative substitutions. The antibodies and bispecific antigen-binding molecules useful herein comprise one or more amino acid substitutions, insertions and/or deletions in the framework and/or CDR regions of the heavy and light chain variable domains as compared to the corresponding germline sequences from which the individual antigen-binding domains were derived, while maintaining or improving the desired antigen-binding characteristics. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present disclosure also includes antigen-binding molecules comprising an antigen-binding domain with an HCVR, LCVR, and/or CDR amino acid sequence that is substantially identical to any of the HCVR, LCVR, and/or CDR amino acid sequences disclosed herein, while maintaining or improving the desired antigen affinity. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, incorporated herein by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence disclosed herein to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Once obtained, antigen-binding domains that contain one or more germline mutations were tested for decreased binding affinity utilizing one or more in vitro assays. Although antibodies that recognize a particular antigen are typically screened for their purpose by testing for high (i.e. strong) binding affinity to the antigen, the antibodies useful herein exhibit weak binding or no detectable binding. Bispecific antigen-binding molecules comprising one or more antigen-binding domains obtained in this general manner are also encompassed within the present disclosure and were found to be advantageous as avidity-driven tumor therapies.

Unexpected benefits, for example, improved pharmacokinetic properties and low toxicity to the patient may be realized from the methods described herein.

Binding Properties of the Antibodies

As used herein, the term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods.* 1997, 201(2):223-31; Geuijen, C A, et al. *J Immunol Methods.* 2005, 302(1-2):68-77).

Accordingly, the antibody or antigen-binding protein disclosed herein binds to the predetermined antigen or cell surface molecule (receptor) having an affinity corresponding to a $K_D$ value that is at least ten-fold lower than its affinity for binding to a non-specific antigen (e.g., BSA, casein). According to the present disclosure, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody disclosed herein.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody disclosed herein that gives half-maximal binding to cells expressing CD3 or tumor-associated antigen, as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Bispecific Antigen-Binding Molecules

The antibodies useful herein may be monospecific, bispecific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-MUC16/anti-CD3 bispecific antibodies useful herein can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

Use of the expression "anti-CD3 antibody" or "anti-MUC16 antibody" herein is intended to include both monospecific anti-CD3 or anti-MUC16 antibodies as well as bispecific antibodies comprising a CD3-binding arm and a MUC16-binding arm. Thus, the present disclosure includes monospecific antibodies which bind MUC16, for example, those anti-MUC16 antibodies described in U.S. 2018/0112001. Exemplary anti-MUC16 antibodies include the H1H8767P antibody and antibodies comprising the CDRs within the H1H8767P antibody as disclosed in U.S. 2018/0112001. In addition, the present disclosure includes bispecific antibodies wherein one arm of an immunoglobulin binds human CD3, and the other arm of the immunoglobulin is specific for human MUC16. Exemplary sequences of the bispecific antibody useful according to the methods provided herein are shown in Table 1.

In certain embodiments, the CD3-binding arm binds to human CD3 and induces human T cell activation. In certain embodiments, the CD3-binding arm binds weakly to human CD3 and induces human T cell activation. In other embodiments, the CD3-binding arm binds weakly to human CD3 and induces tumor-associated antigen-expressing cell killing in the context of a bispecific or multispecific antibody. In other embodiments, the CD3-binding arm binds or associated weakly with human and cynomolgus (monkey) CD3, yet the binding interaction is not detectable by in vitro assays known in the art.

According to certain exemplary embodiments, the present disclosure includes bispecific antigen-binding molecules that specifically bind CD3 and MUC16. Such molecules may be referred to herein as, e.g., "anti-CD3/anti-MUC16," or "anti-CD3×MUC16" or "CD3×MUC16" bispecific molecules, or other similar terminology (e.g., anti-MUC16/anti-CD3).

The term "MUC16," as used herein, refers to the human MUC16 protein unless specified as being from a non-human species (e.g., "mouse MUC16," "monkey MUC16," etc.).

The aforementioned bispecific antigen-binding molecules that specifically bind CD3 and MUC16 may comprise an anti-CD3 antigen-binding molecule which binds to CD3 with a weak binding affinity such as exhibiting a $K_D$ of greater than about 40 nM, as measured by an in vitro affinity binding assay.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present disclosure, the first antigen-binding domain specifically binds a first antigen (e.g., CD3), and the second antigen-binding domain specifically binds a second, distinct antigen (e.g., MUC16).

In certain exemplary embodiments, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule useful herein. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules useful herein will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules useful herein. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules useful herein, the multimerizing domains, e.g., Fc domains, may comprise one or more amino acid changes (e.g., insertions, deletions or substitutions) as compared to the wild-type, naturally occurring version of the Fc domain. For example, the disclosure includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present disclosure also includes bispecific antigen-binding molecules comprising a first Ig $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contain a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 $C_H3$]. These and other examples of chimeric Fc domains that can be included in any of the antigen-binding molecules useful herein are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

pH-Dependent Binding

The present disclosure includes anti-MUC16 antibodies and anti-CD3/anti-MUC16 bispecific antigen-binding molecules with pH-dependent binding characteristics. For example, an anti-MUC16 arm of a bispecific antigen-binding molecule useful herein may exhibit reduced binding to MUC16 at acidic pH as compared to neutral pH. Alternatively, anti-CD3/anti-MUC16 bispecific antigen-binding molecules useful herein may exhibit enhanced binding to MUC16 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to MUC16 at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments useful herein, anti-MUC16 antibodies and anti-CD3/anti-MUC16 bispecific antigen-binding molecules are provided comprising an Fc domain comprising one or more mutations which enhance or diminish antibody binding to the FcRn receptor, e.g., at acidic pH as compared to neutral pH. For example, the present disclosure includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-MUC16 antibodies and anti-CD3/anti-MUC16 bispecific antigen-binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Bispecific Antigen-Binding Molecules

Useful according to the present disclosure are monospecific and bispecific antibodies and antigen-binding fragments thereof that bind CD3-expressing human T-cells and/or human MUC16 with high affinity (e.g., sub-nanomolar $K_D$ values). Such antibodies and their properties are disclosed in U.S. Publication No. 2018/0112001, incorporated by reference herein. Such bispecific antibodies are particularly useful in combination with an anti-4-1BB agonist in the treatment of tumors.

Useful herein are anti-MUC16 antibodies and anti-CD3/anti-MUC16 bispecific antigen-binding molecules which exhibit one or more characteristics selected from the group consisting of: (a) inhibiting tumor growth in immunocompromised mice bearing human ovarian cancer xenografts; and (b); suppressing tumor growth of established tumors in immunocompromised mice bearing human ovarian cancer xenografts (see, e.g., U.S. Publication No. 2018/0112001, Example 8).

Useful herein are antibodies and antigen-binding fragments thereof that bind human CD3 with medium or low affinity, depending on the therapeutic context and particular targeting properties that are desired. For example, in the context of a bispecific antigen-binding molecule, wherein one arm binds CD3 and another arm binds a target antigen (e.g., MUC16), it may be desirable for the target antigen-binding arm to bind the target antigen with high affinity while the anti-CD3 arm binds CD3 with only moderate or low affinity. In this manner, preferential targeting of the antigen-binding molecule to cells expressing the target antigen may be achieved while avoiding general/untargeted CD3 binding and the consequent adverse side effects associated therewith.

The bispecific antigen-binding molecules (e.g., bispecific antibodies) useful herein are capable of simultaneously binding to human CD3 and a human MUC16. The binding arm that interacts with cells that express CD3 may have weak to no detectable binding as measured in a suitable in vitro binding assay. The extent to which a bispecific antigen-binding molecule binds cells that express CD3 and/or MUC16 can be assessed by fluorescence activated cell sorting (FACS), as illustrated in U.S. 2018/0112001, Example 5.

For example, useful herein are bispecific antibodies thereof which specifically bind human T-cell lines which express CD3 but do not express MUC16, e.g., Jurkat and/or primate T-cells (e.g., cynomolgus peripheral blood mononuclear cells [PBMCs]). Also useful herein are bispecific antibodies which bind to MUC16-expressing cells and cell lines, with an $EC_{50}$ value of less than or equal to 7 nM ($7 \times 10^{-9}$), as determined using a FACS binding assay as set forth in U.S. Publication No. 2018/0112001, Example 5, or a substantially similar assay.

In some aspects, the bispecific antibodies bind human CD3 with weak (i.e. low) or even no detectable affinity. According to certain embodiments, the present disclosure includes antibodies and antigen-binding fragments of antibodies that bind human CD3 (e.g., at 37° C.) with a $K_D$ of greater than about 11 nM as measured by surface plasmon resonance.

In some aspects, the bispecific antibodies bind monkey (i.e. cynomolgus) CD3 with weak (i.e. low) or even no detectable affinity.

In some aspects, the bispecific antibodies bind human CD3 and induce T cell activation. For example, certain anti-CD3 antibodies induce human T cell activation with an $EC_{50}$ value of less than about 113 pM, as measured by an in vitro T cell activation assay.

The bispecific antibodies useful herein can bind human CD3 and induce T cell-mediated killing of tumor antigen-expressing cells. For example, the present disclosure includes bispecific antibodies that induce T cell-mediated killing of tumor cells with an $EC_{50}$ of less than about 1.3 nM, as measured in an in vitro T cell-mediated tumor cell killing assay.

The bispecific antibodies useful herein can bind CD3 with a dissociative half-life (t½) of less than about 10 minutes as measured by surface plasmon resonance at 25° C. or 37° C.

The anti-CD3/anti-MUC16 bispecific antigen-binding molecules useful herein may additionally exhibit one or more characteristics selected from the group consisting of: (a) inducing PBMC proliferation in vitro; (b) activating T-cells via inducing IFN-gamma release and CD25 up-regulation in human whole blood; and (c) inducing T-cell mediated cytotoxicity of MUC16 expressing tumor cells.

The present disclosure includes anti-CD3/anti-MUC16 bispecific antigen-binding molecules which are capable of depleting tumor antigen-expressing cells in a subject (see, e.g., U.S. Publication No. 2018/0112001, Example 8). For example, according to certain embodiments, anti-CD3/anti-MUC16 bispecific antigen-binding molecules are provided, wherein a single administration of the bispecific antigen-binding molecule to a subject (e.g., at a dose of about 5.0 mg/kg, about 0.1 mg/kg, about 0.08 mg/kg, about 0.06 mg/kg, about 0.04 mg/kg, about 0.02 mg/kg, about 0.01 mg/kg, or less) causes a reduction in the number of MUC16-expressing cells in the subject (e.g., tumor growth in the subject is suppressed or inhibited) below detectable levels. Unless otherwise indicated, bioluminescent radiance refers to [p/s/cm2²/sr].

In certain embodiments, a single administration of the anti-CD3/anti-MUC16 bispecific antigen-binding molecule at a dose of about 0.4 mg/kg causes a reduction in tumor growth in the subject below detectable levels by about day 7, about day 6, about day 5, about day 4, about day 3, about day 2, or about day 1 after administration of the bispecific antigen-binding molecule to the subject. According to certain embodiments, a single administration of an anti-CD3/anti-MUC16 bispecific antigen-binding molecule disclosed herein, at a dose of at least about 0.01 mg/kg, for example, at least about 85 ug/kg, or at least about 100 ug/kg, causes the number of MUC16-expressing tumor cells to remain below detectable levels until at least about 7 days, 8 days, 9 days, 10 days, 11 days, 12 days, 13 days, 14 days, 15 days, 16 days, 17 days or more, following the administration. As used herein, the expression "below detectable levels" means that no tumor cells can be directly or indirectly detected growing subcutaneously in a subject using standard caliper measurement methods, e.g., as set forth in U.S. Publication No. 2018/0112001 Example 8.

Also useful according to the methods provided herein are anti-CD3/anti-MUC16 bispecific antigen-binding molecules which exhibit one or more characteristics selected from the group consisting of: (a) inhibiting tumor growth in immunocompromised mice bearing human ovarian cancer xenografts; (b) inhibiting tumor growth in immunocompetent mice bearing human ovarian cancer xenografts; (c) suppressing tumor growth of established tumors in immunocompromised mice bearing human ovarian cancer xenografts; and (d) reducing tumor growth of established tumors in immunocompetent mice bearing human ovarian cancer xenografts (see, e.g., U.S. Publication No. 2018/0112001, Example 8). Exemplary anti-CD3/anti-MUC16 bispecific antigen-binding molecules can further exhibit one or more characteristics selected from the group consisting of: (a) induce transient dose-dependent increases in circulating cytokines, (b) induce transient increases in circulating T cells, and (c) do not deplete effector T cell cells (e.g. $CD4^+$ T cells, CD8+ T cells, and regulatory T cells, i.e. Tregs).

Also useful according to the methods provided herein are anti-MUC16 antibody drug conjugates, including anti-MUC16×anti-CD3 bispecific antigen-binding molecule drug conjugates, which inhibit tumor growth in in vivo MUC16 positive ovarian cancer xenograft models (see, e.g., U.S. 2018/0112001, Example 10, in a bioluminescent imaging assay, or a substantially similar assay).

Epitope Mapping and Related Technologies

The epitope on CD3 and/or MUC16 to which the antigen-binding molecules useful herein bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 or MUC16 protein. Alternatively, the epitope may consist of a plurality of non-contiguous amino acids (or amino acid sequences) of CD3 or MUC16. The antibodies useful according to the methods disclosed herein may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

Exemplary bispecific antigen-binding molecules useful herein can comprise a first antigen-binding domain that specifically binds human CD3 and/or cynomolgus CD3 with low or detectable binding affinity, and a second antigen binding domain that specifically binds human MUC16, wherein the first antigen-binding domain binds to the same epitope on CD3 as any of the specific exemplary CD3-specific antigen-binding domains described herein, and/or wherein the second antigen-binding domain binds to the same epitope on MUC16 as any of the specific exemplary MUC16-specific antigen-binding domains described herein.

Likewise, the bispecific antigen-binding molecules useful herein can comprise a first antigen-binding domain that specifically binds human CD3, and a second antigen binding domain that specifically binds human MUC16, wherein the first antigen-binding domain competes for binding to CD3 with any of the specific exemplary CD3-specific antigen-binding domains described herein in Table 1, and/or wherein the second antigen-binding domain competes for binding to MUC16 with any of the specific exemplary MUC16-specific antigen-binding domains described herein in Table 1.

One can easily determine whether a particular antigen-binding molecule (e.g., antibody) or antigen-binding domain thereof binds to the same epitope as, or competes for binding with, a reference antigen-binding molecule of the present disclosure by using routine methods known in the art. For example, to determine if a test antibody binds to the same epitope on MUC16 (or CD3) as a reference bispecific antigen-binding molecule of the present disclosure, the reference bispecific molecule is first allowed to bind to a MUC16 protein (or CD3 protein). Next, the ability of a test antibody to bind to the MUC16 (or CD3) molecule is assessed. If the test antibody is able to bind to MUC16 (or CD3) following saturation binding with the reference bispecific antigen-binding molecule, it can be concluded that the test antibody binds to a different epitope of MUC16 (or CD3) than the reference bispecific antigen-binding molecule. On the other hand, if the test antibody is not able to bind to the MUC16 (or CD3) molecule following saturation binding with the reference bispecific antigen-binding molecule, then the test antibody may bind to the same epitope of MUC16 (or CD3) as the epitope bound by the reference bispecific antigen-binding molecule. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a MUC16 protein (or CD3 protein) under saturating conditions followed by assessment of binding of the test antibody to the MUC16 (or CD3) molecule. In a second orientation, the test antibody is allowed to bind to a MUC16 (or CD3) molecule under saturating conditions followed by assessment of binding of the reference antigen-binding molecule to the MUC16 (or CD3) molecule. If, in both orientations, only the first (saturating) antigen-binding molecule is capable of binding to the MUC16 (or CD3) molecule, then it is concluded that the test antibody and the reference antigen-binding molecule compete for binding to MUC16 (or CD3). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and MUC16), can be appropriately arranged relative to one another to produce a bispecific antigen-binding molecule using routine methods. (A discussion of exemplary bispecific antibody formats that can be used to construct bispecific antigen-binding molecules of the present disclosure is provided elsewhere herein). In certain embodiments, one or more of the individual components (e.g., heavy and light chains) of the multispecific antigen-binding molecules are derived from chimeric, humanized or fully human antibodies. Methods for making such antibodies are well known in the art. For example, one or more of the heavy and/or light chains of the bispecific antigen-binding molecules useful herein can be prepared using VELOCIMMUNE™ technology. Using VELOCIMMUNE™ technology (see, for example, U.S. Pat. No. 6,596,541, Regeneron Pharmaceuticals, VELOCIMMUNE®, or any other human antibody generating technology), high affinity chimeric antibodies to a particular antigen (e.g., CD3 or MUC16) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules useful herein.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., U.S. Pat. No. 10,143,186 for a detailed discussion of such engineered mice and the use thereof to produce bispecific antigen-binding molecules).

Bioequivalents

The presently disclosed methods contemplate the use of antigen-binding molecules having amino acid sequences that vary from those of the exemplary molecules disclosed herein but that retain the ability to bind CD3 and/or MUC16. Such variant molecules may comprise one or more additions, deletions, or substitutions of amino acids when compared to parent sequence, but exhibit biological activity that is essentially equivalent to that of the described bispecific antigen-binding molecules.

Useful herein are antigen-binding molecules that are bioequivalent to any of the exemplary antigen-binding molecules set forth in Table 1. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments, bispecific antigen-binding molecules useful herein bind to human CD3 but not to CD3 from other species. Also useful herein are antigen-binding molecules which bind to human MUC16 but not to MUC16 from other species. The presently disclosed methods also contemplate use of bispecific antigen-binding molecules that bind to human CD3 and to CD3 from one or more non-human species; and/or bispecific antigen-binding molecules that bind to human MUC16 and to MUC16 from one or more non-human species.

According to certain exemplary embodiments, antigen-binding molecules useful herein bind to human CD3 and/or human MUC16 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or MUC16. For example, in a particular exemplary embodiment of the present disclosure bispecific antigen-binding molecules are provided comprising a first antigen-binding domain that binds human CD3 and cynomolgus CD3, and a second antigen-binding domain that specifically binds human MUC16.

Radiolabeled Immunoconjugates of Anti-MUC16/Anti-CD3 Antigen Binding Molecule for Immuno-PET Imaging Provided herein are radiolabeled antigen-binding proteins that bind MUC16 and/or CD3. In some embodiments, the radiolabeled antigen-binding proteins comprise an antigen-binding protein covalently linked to a positron emitter. In some embodiments, the radiolabeled antigen-binding proteins comprise an antigen-binding protein covalently linked to one or more chelating moieties, which are chemical moieties that are capable of chelating a positron emitter.

Suitable radiolabeled antigen-binding proteins, e.g., radiolabeled antibodies, include those that do not impair, or do not substantially impair T-cell function upon exposure to the radiolabeled antigen-binding protein. In some embodiments, a radiolabeled antigen-binding protein that binds an anti-MUC16/anti-CD3 antigen binding molecule is a weak blocker of CD3 T-cell function, i.e. T-cell function is unimpaired, or substantially unimpaired, upon exposure to the radiolabeled antibody. Use of a radiolabeled anti-CD3 binding protein having minimal impact on CD3 mediated T-cell function according to methods provided herein ensures a subject treated with the molecule is not disadvantaged by the inability of its T-cells to clear infection.

In some embodiments, anti-MUC16 antibodies or an anti-MUC16/anti-CD3 antigen binding molecules, e.g., bispecific antibodies, are provided, wherein said antigen-binding proteins are covalently bonded to one or more moieties having the following structure:

-L-M$_Z$ wherein L is a chelating moiety; M is a positron emitter; and z, independently at each occurrence, is 0 or 1; and wherein at least one of z is 1.

In some embodiments, the radiolabeled antigen-binding protein is a compound of Formula (I):

M-L-A-[L-M$_Z$]$_k$                                       (I)

A is an anti-MUC16 antibody or an anti-MUC16/anti-CD3 antigen binding molecule; L is a chelating moiety; M is a positron emitter; z is 0 or 1; and k is an integer from 0-30. In some embodiments, k is 1. In some embodiments, k is 2.

In certain embodiments, the radiolabeled antigen-binding protein is a compound of Formula (II):

A-[L-M]$_k$ wherein A is an anti-MUC16 antibody or an anti-MUC16/anti-CD3 antigen binding molecule; L is a chelating moiety; M is a positron emitter; and k is an integer from 1-30.

In some embodiments, provided herein are compositions comprising a conjugate having the following structure:

A-L$_k$ wherein A is an anti-MUC16 antibody or an anti-MUC16/anti-CD3 antigen binding molecule; L is a chelating moiety; and k is an integer from 1-30; wherein the conjugate is chelated with a positron emitter in an amount sufficient to provide a specific activity suitable for clinical PET imaging.

Suitable chelating moieties, and positron emitters are provided below.

Positron Emitters and Chelating Moieties

Suitable positron emitters include, but are not limited to, those that form stable complexes with the chelating moiety and have physical half-lives suitable for immuno-PET imaging purposes. Illustrative positron emitters include, but are not limited to, $^{89}$Zr, $^{68}$Ga, $^{64}$Cu, $^{44}$Sc, and $^{86}$Y. Suitable positron emitters also include those that directly bond with the anti-MUC16 antibody or the anti-MUC16/anti-CD3 bispecific antigen binding molecule, including, but not limited to, $^{76}$Br and $^{124}$I, and those that are introduced via prosthetic group, e.g., $^{18}$F.

The chelating moieties described herein are chemical moieties that are covalently linked to the anti-MUC16 antibody or anti-MUC16/anti-CD3 antigen binding molecule and comprise a portion capable of chelating a positron emitter, i.e., capable of reacting with a positron emitter to form a coordinated chelate complex. Suitable moieties include those that allow efficient loading of the particular metal and form metal-chelator complexes that are sufficiently stable in vivo for diagnostic uses, e.g., immuno-PET imaging. Illustrative chelating moieties include those that minimize dissociation of the positron emitter and accumulation in mineral bone, plasma proteins, and/or bone marrow depositing to an extent suitable for diagnostic uses.

Examples of chelating moieties include, but are not limited to, those that form stable complexes with positron emitters $^{89}$Zr, $^{68}$Ga, $^{64}$Cu, $^{44}$Sc, and/or $^{86}$Y. Illustrative chelating moieties include, but are not limited to, those described in *Nature Protocols*, 5(4): 739, 2010; *Bioconjugate Chem.*, 26(12): 2579 (2015); *Chem Commun (Camb)*, 51(12): 2301 (2015); *Mol. Pharmaceutics*, 12: 2142 (2015); *Mol. Imaging Biol.*, 18: 344 (2015); *Eur. J. Nucl. Med. Mol. Imaging*, 37:250 (2010); *Eur. J. Nucl. Med. Mol. Imaging* (2016). doi:10.1007/s00259-016-3499-x; *Bioconjugate Chem.*, 26(12): 2579 (2015); WO 2015/140212A1; and U.S. Pat. No. 5,639,879, incorporated by reference in their entireties.

Illustrative chelating moieties also include, but are not limited to, those that comprise desferrioxamine (DFO), 1,4,7,10-tetraacetic acid (DOTA), diethylenetriaminepentaacetic acid (DTPA), ethylenediaminetetraacetic acid (EDTA), (1,4,7,10-Tetraazacyclododecane-1,4,7,10-tetra (methylene phosphonic) acid (DOTP), 1R, 4R, 7R, 10R)-α'α"α'"-Tetramethyl-1,4,7,10-tetraazacyclododecane-1,4,7,10-tetraacetic acid (DOTMA), 1,4,8,11-Tetraazacyclotetradecane-1,4,8, 11-tetraacetic acid (TETA), H$_4$octapa, H$_6$phospa, H$_2$dedpa, H$_5$decapa, H$_2$azapa, HOPO, DO2A, 1,4,7,10-Tetrakis(carbamoylmethyl)-1,4,7,10-tetraazacyclododecane (DOTAM), 1,4,7-triazacyclononane-N, N',N"-triacetic acid (NOTA), 1,4,7,10-Tetrakis(carbamoylmethyl)-1,4,7,10-tetraazacyclododecane (DOTAM), 1,4,8, 11-tetraazabicyclo[6.6.2]hexadecane-4, 11-dicetic acid (CB-TE2A), 1,4,7,10-Tetraazacyclododecane (Cyclen), 1,4,8,11-Tetraazacyclotetradecane (Cyclam), octadentate chelators, octadentate bifunctional chelating agents, e.g., DFO*, hexadentate chelators, phosphonate-based chelators, macrocyclic chelators, chelators comprising macrocyclic terephthalamide ligands, bifunctional chelators, fusarinine C and fusarinine C derivative chelators, triacetylfusarinine C (TAFC), ferrioxamine E (FOXE), ferrioxamine B (FOXB), ferrichrome A (FCHA), and the like.

In some embodiments, the chelating moieties are covalently bonded to the anti-MUC16 antibody or anti-MUC16/anti-CD3 bispecific antigen binding molecule, via a linker moiety, which covalently attaches the chelating portion of the chelating moiety to the binding protein. In some embodiments, these linker moieties are formed from a reaction between a reactive moiety of the bispecific antigen binding molecule, e.g., cysteine or lysine of an antibody, and reactive moiety that is attached to a chelator, including, for example, a p-isothiocyanatobenyl group and the reactive moieties provided in the conjugation methods below. In addition, such linker moieties optionally comprise chemical groups used for purposes of adjusting polarity, solubility, steric interactions, rigidity, and/or the length between the chelating portion and the anti-MUC16 antibody or anti-MUC16/anti-CD3 bispecific antigen binding molecule.

Preparation of Radiolabeled Anti-MUC16/Anti-CD3 Bispecific Antigen Binding Molecule Conjugates The radiolabeled anti-MUC16 antibody conjugates and anti-MUC16/anti-CD3 bispecific antigen binding molecule conjugates can be prepared by (1) reacting the antigen binding molecule with a molecule comprising a positron emitter chelator and a moiety reactive to the desirable conjugation site of the bispecific binding protein and (2) loading the desirable positron emitter.

Suitable conjugation sites include, but are not limited to, lysine and cysteine, both of which can be, for example, native or engineered, and can be, for example, present on the heavy or light chain of an antibody. Cysteine conjugation sites include, but are not limited to, those obtained from mutation, insertion, or reduction of antibody disulfide bonds. Methods for making cysteine engineered antibodies include, but are not limited to, those disclosed in WO2011/056983. Site-specific conjugation methods can also be used to direct the conjugation reaction to specific sites of an antibody, achieve desirable stoichiometry, and/or achieve desirable chelator-to-antibody ratios. Such conjugation methods are known to those of ordinary skill in the art and include, but are not limited to, cysteine engineering and enzymatic and chemo-enzymatic methods, including, but not limited to, glutamine conjugation, Q295 conjugation, and transglutaminase-mediated conjugation, as well as those described in *J.Clin.Immunol.*, 36: 100 (2016), incorporated herein by reference in its entirety. Suitable moieties reactive to the desirable conjugation site generally enable efficient and facile coupling of the anti-MUC16/anti-CD3 bispecific antigen binding molecule, e.g., bispecific antibody and positron emitter chelator. Moieties reactive to lysine and cysteine sites include electrophilic groups, which are known to those of ordinary skill. In certain aspects, when the desired conjugation site is lysine, the reactive moiety is an isothiocyanate, e.g., p-isothiocyanatobenyl group or reactive ester. In certain aspects, when the desired conjugation site is cysteine, the reactive moiety is a maleimide.

When the chelator is desferrioxamine (DFO), suitable reactive moieties include, but are not limited to, an isothiocyantatobenzyl group, an n-hydroxysuccinimide ester,2,3, 5,6 tetrafluorophenol ester, n-succinimidyl-S-acetylthioacetate, and those described in *BioMed Research International*, Vol 2014, Article ID 203601, incorporated herein by reference in its entirety. In certain embodiments, the molecule comprising a positron emitter chelator and moiety reactive to the conjugation site is p-isothiocyantatobenzyl-desferrioxamine (p-SCN-Bn-DFO):

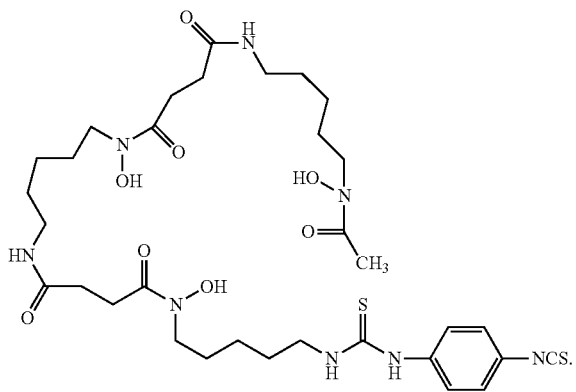

Positron emitter loading is accomplished by incubating the anti-MUC16 antibody or anti-MUC16/anti-CD3 bispecific antigen binding molecule chelator conjugate with the positron emitter for a time sufficient to allow coordination of said positron emitter to the chelator, e.g., by performing the methods described in the examples provided herein, or substantially similar method.

Illustrative Embodiments of Conjugates

Included in the instant disclosure are radiolabeled antibody conjugates comprising an anti-MUC16 antibody or an anti-MUC16/anti-CD3 bispecific antigen binding molecule and a positron emitter. Also included in the instant disclosure are radiolabeled antibody conjugates comprising an anti-MUC16 antibody or an anti-MUC16/anti-CD3 bispecific antigen binding molecule, a chelating moiety, and a positron emitter. (Tavare et al. Cancer Res. 2016, 76(1): 73-82; and Azad et al. Oncotarget. 2016, 7(11): 12344-58.)

In some embodiments, the chelating moiety comprises a chelator capable of forming a complex with $^{89}$Zr. In certain embodiments, the chelating moiety comprises desferrioxamine. In certain embodiments, the chelating moiety is p-isothiocyanatobenzyl-desferrioxamine.

In some embodiments, the positron emitter is $^{89}$Zr. In some embodiments, less than 1.0% of the anti-MUC16 antibody or anti-MUC16/anti-CD3 bispecific antigen binding molecule is conjugated with the positron emitter, less than 0.9% of the anti-MUC16 antibody or anti-MUC16/anti-CD3 bispecific antigen binding molecule is conjugated with the positron emitter, less than 0.8% of the anti-MUC16 antibody or anti-MUC16/anti-CD3 bispecific antigen binding molecule is conjugated with the positron emitter, less than 0.7% of the anti-MUC16 antibody or anti-MUC16/anti-CD3 bispecific antigen binding molecule is conjugated with the positron emitter, less than 0.6% of the anti-MUC16 antibody or anti-MUC16/anti-CD3 bispecific antigen binding molecule is conjugated with the positron emitter, less than 0.5% of the anti-MUC16 antibody or anti-MUC16/anti-CD3 bispecific antigen binding molecule is conjugated with the positron emitter, less than 0.4% of the anti-MUC16 antibody or anti-MUC16/anti-CD3 bispecific antigen binding molecule is conjugated with the positron emitter, less than 0.3% of the anti-MUC16 antibody or anti-MUC16/anti-CD3 bispecific antigen binding molecule is conjugated with the positron emitter, less than 0.2% of the anti-MUC16 antibody or anti-MUC16/anti-CD3 bispecific antigen binding molecule is conjugated with the positron emitter, or less than 0.1% of the anti-MUC16 antibody or anti-MUC16/anti-CD3 bispecific antigen binding molecule is conjugated with the positron emitter.

In some embodiments, the chelating moiety-to-antibody ratio of the conjugate is from 1.0 to 2.0. As used herein, "chelating moiety-to-antibody ratio" is the average chelator moiety to antibody ratio and is a measure of chelator load per antibody. This ratio is analogous to "DAR", i.e., drug-antibody ratio, which is used by those skilled in the art to measure drug load per antibody for antibody-drug conjugates (ADCs); in the context of the conjugates described herein for iPET imaging, the chelating moiety-to-antibody ratio can be ascertained using methods described herein and others known in the art for the determination of DAR, e.g. those described in Wang et al., Antibody-Drug Conjugates, The 21$^{st}$ Century Magic Bullets for Cancer (2015). In some embodiments, the chelating moiety-to-antibody ratio is about 1.7. In some embodiments, the chelating moiety-to-antibody ratio is from 1.0 to 2.0. In some embodiments, the chelating moiety-to-antibody ratio is about 1.7.

In a particular embodiment, the chelating moiety is p-isothiocyanatobenzyl-desferrioxamine and the positron emitter is $^{89}$Zr. In another particular embodiment, the chelating moiety is p-isothiocyanatobenzyl-desferrioxamine and the positron emitter is $^{89}$Zr, and the chelating moiety-to-antibody ratio of the conjugate is from 1 to 2.

In some embodiments, provided herein are anti-MUC16 antibodies or anti-MUC16/anti-CD3 bispecific antigen binding molecules, wherein said antigen-binding molecules are covalently bonded to one or more moieties having the following structure:

-L-M$_Z$ wherein L is a chelating moiety; M is a positron emitter; and z, independently at each occurrence, is 0 or 1; and wherein at least one of z is 1. In certain embodiments, the radiolabeled antigen-binding protein is a compound of Formula (I):

M-L-A-[L-M$_Z$]$_k$          (I)

A is an anti-MUC16 antibody or an anti-MUC16/anti-CD3 bispecific antigen binding molecule; L is a chelating moiety;

M is a positron emitter; z is 0 or 1; and k is an integer from 0-30. In some embodiments, k is 1. In some embodiments, k is 2.

In some embodiments, L is:

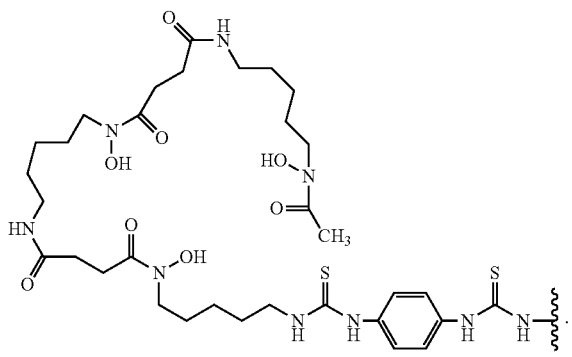 [SMILES: *NC(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, M is $^{89}$Zr.

In some embodiments, k is an integer from 1 to 2. In some embodiments, k is 1. In some embodiments, k is 2.

In some embodiments, -L-M is

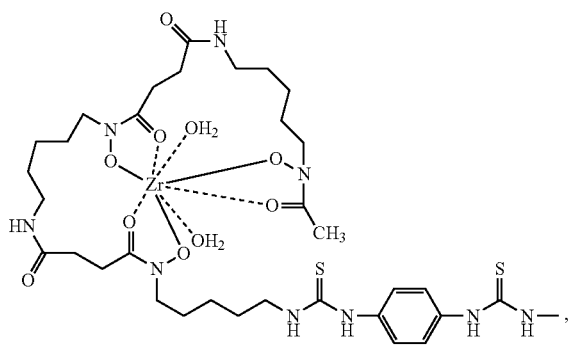

wherein Zr is the positron emitter $^{89}$Zr.

Included in the instant disclosure are also methods of synthesizing a radiolabeled antibody conjugate comprising contacting a compound of Formula (III):

(III)

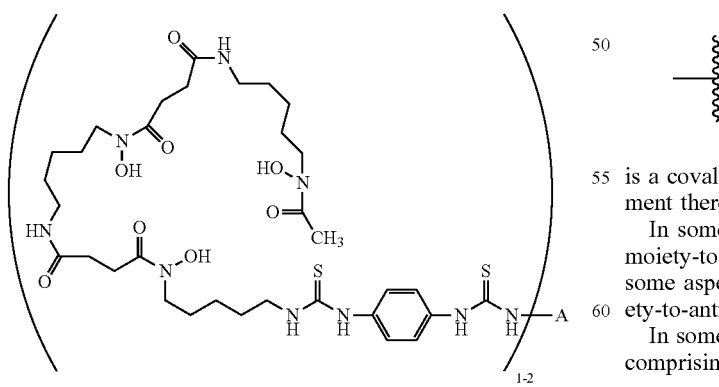

with $^{89}$Zr, wherein A is an anti-MUC16 antibody or an anti-MUC16/anti-CD3 bispecific antigen binding molecule. In certain embodiments, the compound of Formula (III) is synthesized by contacting the anti-MUC16 antibody or anti-MUC16/anti-CD3 bispecific antigen binding molecule with p-SCN-Bn-DFO.

Provided herein is also the product of the reaction between a compound of Formula (III) with $^{89}$Zr.

Provided herein are compounds of Formula (III):

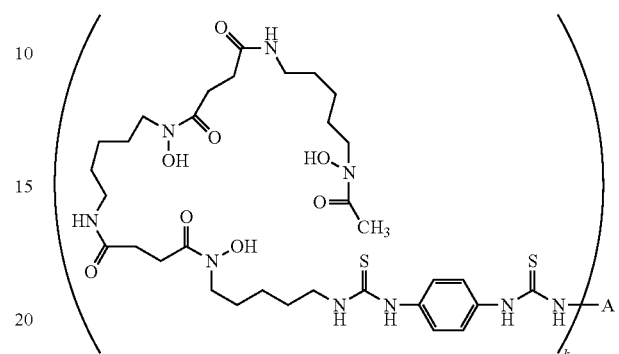

wherein A is an anti-MUC16 antibody or an anti-MUC16/anti-CD3 bispecific antigen binding molecule and k is an integer from 1-30. In some embodiments, k is 1 or 2.

Provided herein are antibody conjugates comprising (i) an anti-MUC16 antibody or an anti-MUC16/anti-CD3 bispecific antigen binding molecule and (ii) one or more chelating moieties.

In some embodiments, the chelating moiety comprises:

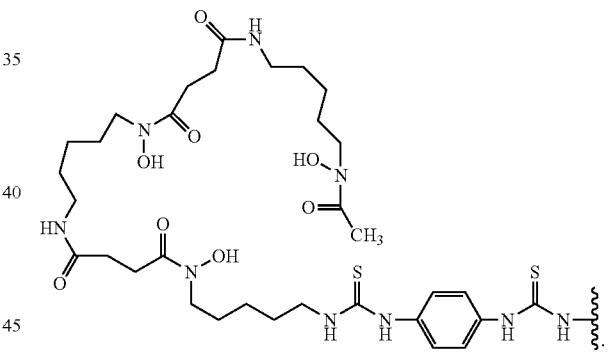

is a covalent bond to the antibody or antigen-binding fragment thereof.

In some aspects, the antibody conjugate has a chelating moiety-to-antibody ratio of from about 1.0 to about 2.0. In some aspects, the antibody conjugate has a chelating moiety-to-antibody ratio of about 1.7.

In some embodiments, provided herein are compositions comprising a conjugate having the following structure:

$$A\text{-}L_k$$

wherein A is an anti-MUC16 antibody or an anti-MUC16/anti-CD3 bispecific antigen binding molecule; L is a chelating moiety; and k is an integer from 1-30; the conjugate is chelated with a positron emitter in an amount sufficient to provide a specific activity suitable for clinical PET imaging. In some embodiments, the amount of chelated positron emitter is an amount sufficient to provide a specific activity of about 1 to about 50 mCi per 1-50 mg of the anti-MUC16 antibody or anti-MUC16/anti-CD3 bispecific antigen binding molecule.

In some embodiments, the amount of chelated positron emitter is an amount sufficient to provide a specific activity of up to 50 mCi, up to 45 mCi, up to 40 mCi, up to 35 mCi, up to 30 mCi, up to 25 mCi, or up to 10 mCi per 1-50 mg of the anti-MUC16/anti-CD3 bispecific antigen binding molecule, for example, in a range of about 5 to about 50 mCi, about 10 to about 40 mCi, about 15 to about 30 mCi, about 7 to about 25 mCi, about 20 to about 50 mCi, or about 5 to about 10 mCi.

Methods of Using Radiolabeled Immunoconjugates

In certain aspects, the present disclosure provides diagnostic and therapeutic methods of use of the radiolabeled antibody conjugates of the present disclosure.

According to one aspect, the present disclosure provides methods of detecting MUC16 in a tissue, the methods comprising administering a radiolabeled anti-MUC16 antibody conjugate or anti-MUC16/anti-CD3 bispecific antigen binding molecule conjugate provided herein to the tissue; and visualizing the MUC16 expression by positron emission tomography (PET) imaging. In certain embodiments, the tissue comprises cells or cell lines. In certain embodiments, the tissue is present in a subject, wherein the subject is a mammal. In certain embodiments, the subject is a human subject. In certain embodiments, the subject has a disease or disorder selected from the group consisting of cancer that expresses the MUC16 antigen such as ovarian cancer, breast cancer, pancreatic cancer, endometrial cancer, fallopian tube cancer, mesothelioma, non-small-cell lung cancer, intrahepatic cholangiocarcinoma-mass forming type, adenocarcinoma of the uterine cervix, and adenocarcinoma of the gastric tract. In one embodiment, the subject has ovarian cancer.

According to one aspect, the present disclosure provides methods of imaging a tissue that expresses MUC16 comprising administering a radiolabeled anti-MUC16 antibody conjugate or anti-MUC16/anti-CD3 bispecific antigen binding molecule conjugate of the present disclosure to the tissue; and visualizing the MUC16 expression by positron emission tomography (PET) imaging. In one embodiment, the tissue is comprised in a tumor. In one embodiment, the tissue is comprised in a tumor cell culture or tumor cell line. In one embodiment, the tissue is comprised in a tumor lesion in a subject. In one embodiment, the tissue is intratumoral lymphocytes in a tissue. In one embodiment, the tissue comprises MUC16-expressing cells.

According to one aspect, the present disclosure provides methods for determining if a subject having a tumor is suitable for anti-tumor therapy, the methods comprising administering a radiolabeled antibody conjugate of the present disclosure, and localizing the administered radiolabeled antibody conjugate in the tumor by PET imaging wherein presence of the radiolabeled antibody conjugate in the tumor identifies the subject as suitable for anti-tumor therapy.

According to one aspect, the present disclosure provides methods for predicting response of a subject having a solid tumor to an anti-tumor therapy, the methods comprising determining if the tumor is MUC16 positive, wherein a positive response of the subject is predicted if the tumor is MUC16 positive. In certain embodiments, the tumor is determined positive by administering a radiolabeled antibody conjugate of the present disclosure and localizing the radiolabeled antibody conjugate in the tumor by PET imaging wherein presence of the radiolabeled antibody conjugate in the tumor indicates that the tumor is MUC16 positive.

According to one aspect, the present disclosure provides methods for detecting a MUC16 positive tumor in a subject. The methods, according to this aspect, comprise administering a radiolabeled antibody conjugate of the present disclosure to the subject; and determining localization of the radiolabeled antibody conjugate by PET imaging, wherein presence of the radiolabeled antibody conjugate in a tumor indicates that the tumor is MUC16 positive.

Provided herein are methods for predicting a positive response to an anti-tumor therapy comprising: administering a radiolabeled anti-MUC16 antibody conjugate or anti-MUC16/anti-CD3 bispecific antigen binding molecule conjugate to the subject to determine the presence of MUC16 positive cells in the solid tumor. The presence of MUC16-positive cells predicts a positive response to an anti-tumor therapy.

As used herein, the expression "a subject in need thereof" means a human or non-human mammal that exhibits one or more symptoms or indications of cancer, and/or who has been diagnosed with cancer, including a solid tumor and who needs treatment for the same. In many embodiments, the term "subject" may be interchangeably used with the term "patient". For example, a human subject may be diagnosed with a primary or a metastatic tumor and/or with one or more symptoms or indications including, but not limited to, unexplained weight loss, general weakness, persistent fatigue, loss of appetite, fever, night sweats, bone pain, shortness of breath, swollen abdomen, chest pain/pressure, enlargement of spleen, and elevation in the level of a cancer-related biomarker (e.g., CA125). The expression includes subjects with primary or established tumors. In specific embodiments, the expression includes human subjects that have and/or need treatment for a solid tumor, e.g., ovarian cancer, breast cancer, pancreatic cancer, endometrial cancer, fallopian tube cancer, mesothelioma, non-small-cell lung cancer, intrahepatic cholangiocarcinoma-mass forming type, adenocarcinoma of the uterine cervix, and adenocarcinoma of the gastric tract. The term includes subjects with primary or metastatic tumors (advanced malignancies). In certain embodiments, the expression "a subject in need thereof" includes subjects with a solid tumor that is resistant to or refractory to or is inadequately controlled by prior therapy (e.g., treatment with an anti-cancer agent). For example, the expression includes subjects who have been treated with one or more lines of prior therapy such as treatment with chemotherapy (e.g., carboplatin or docetaxel). In certain embodiments, the expression "a subject in need thereof" includes subjects with a solid tumor which has been treated with one or more lines of prior therapy but which has subsequently relapsed or metastasized.

In certain embodiments, the methods of the present disclosure are used in a subject with a solid tumor. The terms "tumor", "cancer" and "malignancy" are interchangeably used herein. As used herein, the term "solid tumor" refers to an abnormal mass of tissue that usually does not contain cysts or liquid areas. Solid tumors may be benign (not cancer) or malignant (cancer). For the purposes of the present disclosure, the term "solid tumor" means malignant solid tumors. The term includes different types of solid tumors named for the cell types that form them, viz. sarcomas, carcinomas and lymphomas.

In certain embodiments, the cancer or tumor is a selected from the group consisting of astrocytoma, anal cancer, bladder cancer, blood cancer, blood cancer, bone cancer, brain cancer, breast cancer, cervical cancer, clear cell renal cell carcinoma, colorectal cancer, microsatellite-intermediate colorectal cancer, cutaneous squamous cell carcinoma, diffuse large B-cell lymphoma, endometrial cancer, esophageal cancer, fallopian tube cancer, mesothelioma, fibrosarcoma, gastric cancer, glioblastoma, glioblastoma multiforme, head and neck squamous cell carcinoma, hepatic cell carcinoma, intrahepatic cholangiocarcinoma-mass forming type, leukemia, liver cancer, leiomyosarcoma, lung cancer, lymphoma, melanoma, mesothelioma, myeloma, nasopharyngeal cancer, non-small cell lung cancer, osteosarcoma, ovarian cancer, pancreatic cancer, pancreatic ductal adenocarcinoma, primary and/or recurrent cancer, prostate cancer, renal cell carcinoma, rhabdomyosarcoma, salivary gland cancer, skin cancer, small cell lung cancer, squamous cell cancer, stomach cancer, synovial sarcoma, testicular cancer, thyroid cancer, triple negative breast cancer, uterine cancer including adenocarcinoma of the uterine cervix, and Wilms' tumor. In some aspects, the cancer is a primary cancer. In some aspects, the cancer is metastatic and/or recurrent cancer.

In certain embodiments, the cancer or tumor is selected from a MUC16 positive tumor, such as a tumor originating in the ovary, breast, bronchia, endometrium, cornea, gastric epithelium, pancreas, or colorectum. In some aspects, the cancer is breast cancer, ovarian cancer, corneal cancer, pancreatic cancer, endometrial cancer, fallopian tube cancer, mesothelioma, non-small cell lung cancer, intrahepatic cholangiocarcinoma-mass forming type, uterine cancer, cervical cancer, gastric cancer, or colorectal carcinoma. In some aspects, the cancer is ovarian cancer. In some aspects, the cancer is metastatic cancer originating from a primary ovarian tumor.

As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, to prevent or inhibit metastasis, to inhibit metastatic tumor growth, and/or to increase duration of survival of the subject.

In certain embodiments, the radiolabeled anti-MUC16 antibody conjugate or anti-MUC16/anti-CD3 bispecific antigen binding molecule conjugate is administered intravenously, intraperitoneally, or subcutaneously to the subject. In certain embodiments, the radiolabeled antibody conjugate is administered intra-tumorally. Upon administration, the radiolabeled antibody conjugate is localized in the tumor. The localized radiolabeled antibody conjugate is imaged by PET imaging and the uptake of the radiolabeled antibody conjugate by the tumor is measured by methods known in the art. In certain embodiments, the imaging is carried out 1, 2, 3, 4, 5, 6 or 7 days after administration of the radiolabeled conjugate. In certain embodiments, the imaging is carried out on the same day upon administration of the radiolabeled antibody conjugate.

In certain embodiments, the radiolabeled anti-MUC16 antibody conjugate or anti-MUC16/anti-CD3 bispecific antigen binding molecule conjugate can be administered at a dose of about 0.1 mg/kg of body weight to about 100 mg/kg of body weight of the subject, for example, about 0.1 mg/kg to about 50 mg/kg, or about 0.5 mg/kg to about 25 mg/kg, or about 0.1 mg/kg to about 1.0 mg/kg of body weight.

Therapeutic Formulation and Administration

Useful according to the present disclosure are pharmaceutical compositions comprising the antigen-binding molecules useful herein. In some aspects, the pharmaceutical composition further comprises an anti-4-1BB agonist. The pharmaceutical compositions are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule is used for therapeutic purposes in an adult patient, it may be advantageous to intravenously administer the bispecific antigen-binding molecule normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

The dose of anti-4-1BB agonist administered to a patient may vary depending upon the age and the size of the patient, target disease, conditions, route of administration, and the like. The preferred dose is typically calculated according to body weight or body surface area. When an anti-4-1BB agonist is used for therapeutic purposes in an adult patient, it may be advantageous to intravenously administer the agonist normally at a single dose of about 0.01 to about 20 mg/kg body weight, more preferably about 0.02 to about 7, about 0.03 to about 5, or about 0.05 to about 3, or about 2.5 mg/kg body weight.

Various delivery systems are known and can be used to administer the pharmaceutical composition useful herein, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition useful herein can be delivered subcutaneously or intravenously with a standard needle and syringe. In addition, with respect to subcutaneous delivery, a pen delivery device readily has applications in delivering a pharmaceutical composition useful herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition useful herein. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTI-CLIK™ (sanofi-aventis, Frankfurt, Germany), to name only a few. Examples of disposable pen delivery devices having applications in subcutaneous delivery of a pharmaceutical composition useful herein include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 1 to about 500 mg per dosage form in a unit dose; especially in the form of injection, it is preferred that the aforesaid antibody is contained in about 1 to about 300 mg and in about 10 to about 500 mg for the other dosage forms.

Combination Therapies and Formulations

The present disclosure provides methods which comprise administering a pharmaceutical composition comprising any of the exemplary monospecific or bispecific antigen-binding molecules described herein in combination with an anti-4-1BB agonist, and one or more additional therapeutic agents. Exemplary additional therapeutic agents that may be combined with or administered in combination with an anti-4-1BB agonist and a bispecific antigen-binding molecule useful herein include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-6 antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 (PSMA) antagonist, a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), etc. Other agents that may be beneficially administered in combination with the compositions provided herein include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions useful herein (e.g., pharmaceutical compositions comprising an anti-CD3/anti-MUC16 bispecific antigen-binding molecule as disclosed herein) may also be administered as part of a therapeutic regimen comprising an anti-4-1 BB agonist and one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present disclosure also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')2 fragment; Fd fragment; Fv fragment; scFv; dAb fragment; or other engineered molecules, such as diabodies, triabodies, tetrabodies, minibodies and minimal recognition units). The antigen-binding molecules disclosed herein may also be administered and/or co-formulated in combination with antivirals, antibiotics, analgesics, corticosteroids and/or NSAIDs. The antigen-binding molecules disclosed herein may also be administered as part of a treatment regimen that also includes radiation treatment and/or conventional chemotherapy.

The additional therapeutically active component(s) may be administered just prior to, concurrent with, or shortly after the administration of an antigen-binding molecule useful herein; (for purposes of the present disclosure, such administration regimens are considered the administration of an antigen-binding molecule "in combination with" an additional therapeutically active component).

The present disclosure includes pharmaceutical compositions in which an antigen-binding molecule useful herein is co-formulated with one or more of the additional therapeutically active component(s) as described elsewhere herein.

Administration Regimens

According to certain embodiments of the present disclosure, multiple doses of an antigen-binding molecule (e.g., an anti-MUC16 antibody or an anti-CD3/anti-MUC16 bispecific antigen-binding molecule) may be administered to a subject over a defined time course. In addition, multiple doses of an anti-4-1BB agonist may be administered to a subject over a defined time course. The methods according to this aspect comprise sequentially administering to a subject one or more doses of each therapeutic, i.e. one or more doses of an antigen-binding molecule and one or more doses of an anti-4-1BB agonist. As used herein, "sequentially administering" means that each dose of a therapeutic, e.g., an antigen-binding molecule, is administered to the subject at a different point in time, e.g., on different days separated by a predetermined interval (e.g., hours, days, weeks or months). The present disclosure includes methods which comprise sequentially administering to the patient a single initial dose of an antigen-binding molecule, referred to as a loading dose, followed by one or more secondary doses of the antigen-binding molecule, and optionally followed by one or more tertiary doses of the antigen-binding molecule. The present disclosure includes methods which comprise sequentially administering to the patient a single initial dose of an anti-4-1BB agonist, referred to as a loading dose, followed by one or more secondary doses of the anti-4-1 BB agonist, and optionally followed by one or more tertiary doses of the anti-4-1BB agonist.

The terms "initial dose," "secondary doses," and "tertiary doses," refer to the temporal sequence of administration of the antigen-binding molecule and/or anti-4-1BB agonist useful herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule (or anti-4-1 BB agonist), but generally may differ from one another in terms of frequency of administration. In certain embodiments, however, the amount of an antigen-binding molecule (or anti-4-1 BB agonist) contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule (or anti-4-1 BB agonist) which is administered to a patient prior to the administration of the very next dose in the sequence with no intervening doses.

The methods according to this aspect of the disclosure may comprise administering to a patient any number of secondary and/or tertiary doses of an anti-4-1 BB agonist, an anti-MUC16 antibody, or a bispecific antigen-binding molecule that specifically binds MUC16 and CD3. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The bispecific antibodies of the present disclosure may also be used to detect and/or measure MUC16, or MUC16-expressing cells in a sample, e.g., for diagnostic purposes. For example, an anti-MUC16 antibody, or fragment thereof, may be used to diagnose a condition or disease characterized by aberrant expression (e.g., over-expression, under-expression, lack of expression, etc.) of MUC16. Exemplary diagnostic assays for MUC16 may comprise, e.g., contacting a sample obtained from a patient with an anti-MUC16 antibody or anti-MUC16×CD3 bispecific antibody, wherein the antibody is labeled with a detectable label or reporter molecule. Alternatively, an unlabeled anti-MUC16 antibody or anti-MUC16×CD3 bispecific antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Another exemplary diagnostic use of the anti-MUC16×CD3 bispecific antibodies useful herein includes $^{89}$Zr-labeled, such as $^{89}$Zr-desferrioxamine-labeled, antibody for the purpose of noninvasive identification and tracking of tumor cells in a subject (e.g. positron emission tomography (PET) imaging). (See, e.g., Tavare, R. et al. Cancer Res. 2016 Jan. 1; 76(1):73-82; and Azad, B B. et al. Oncotarget. 2016 Mar. 15; 7(11):12344-58.) Specific exemplary assays that can be used to detect or measure MUC16 in a sample include enzyme-linked immunosorbent assay (ELISA), radioimmunoassay (RIA), and fluorescence-activated cell sorting (FACS).

Samples that can be used in MUC16 diagnostic assays according to the present disclosure include any tissue or fluid sample obtainable from a patient which contains detectable quantities of MUC16 protein, or fragments thereof, under normal or pathological conditions. Generally, levels of MUC16 in a particular sample obtained from a healthy patient (e.g., a patient not afflicted with a disease or condition associated with abnormal MUC16 levels or activity) will be measured to initially establish a baseline, or standard, level of MUC16. This baseline level of MUC16 can then be compared against the levels of MUC16 measured in samples obtained from individuals suspected of having a MUC16 related disease (e.g., a tumor containing MUC16-expressing cells) or condition.

EXAMPLES

The following examples are put forth so as to provide those of ordinary skill in the art with a complete disclosure and description of how to make and use the methods and compositions useful herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Bispecific Antibodies that Bind MUC16 and CD3

The present disclosure provides anti-MUC16 antibodies useful according to the methods disclosed herein. The antibodies were generated according to the disclosure provided in U.S. 2018/0112001. Exemplary antibodies useful herein include the H1H8767P antibody, and the CDR, HCVR, and LCVR sequences encompassed by this antibody. As such, an exemplary anti-MUC16 antibody or antigen-binding fragment thereof comprises an HCVR of SEQ ID NO: 18 (SEQ ID NO: 1, herein) and an LCVR of SEQ ID NO: 26 (SEQ ID NO: 3, herein) as disclosed in U.S. 2018/0112001.

The present disclosure also provides bispecific antigen-binding molecules that bind CD3 and Mucin 16 (MUC16); such bispecific antigen-binding molecules are also referred to herein as "anti-MUC16/anti-CD3 bispecific molecules." The anti-MUC16 portion of the anti-MUC16/anti-CD3 bispecific molecule is useful for targeting tumor cells that express MUC16, and the anti-CD3 portion of the bispecific molecule is useful for activating T-cells. The simultaneous binding of MUC16 on a tumor cell and CD3 on a T-cell facilitates directed killing (cell lysis) of the targeted tumor cell by the activated T-cell.

Bispecific antibodies comprising an anti-MUC16-specific binding domain and an anti-CD3-specific binding domain were constructed using standard methodologies, wherein the anti-MUC16 antigen binding domain and the anti-CD3 antigen binding domain each comprise different, distinct HCVRs paired with a common LCVR. In exemplified bispecific antibodies, the molecules were constructed utilizing a heavy chain from an anti-CD3 antibody, a heavy chain from an anti-MUC16 antibody and a common light chain from the anti-MUC16 antibody. In other instances, the bispecific antibodies may be constructed utilizing a heavy chain from an anti-CD3 antibody, a heavy chain from an anti-MUC16 antibody and a light chain from an anti-CD3 antibody or an antibody light chain known to be promiscuous or pair effectively with a variety of heavy chain arms.

A summary of the component parts of an exemplary anti-MUC16×CD3 bispecific antibody construct is set forth in Table 1.

TABLE 1

| Anti-MUC16xCD3 Bispecific Antigen Binding Molecule | | | |
|---|---|---|---|
| BSMUC16/CD3-001 | MUC16-binding arm heavy chain | CD3-binding arm heavy chain | Common light chain |
| Antibody VRs | H1H8767P SEQ ID NO: 1 | CD3-VH-G SEQ ID NO: 2 | H1H8767P SEQ ID NO: 3 |
| Full-length sequence | SEQ ID NO: 4 | SEQ ID NO: 5 | SEQ ID NO: 6 |

Example 2: Xenogeneic Ascites Model with OVCAR-3 Cells Expressing Luciferase

The in vivo efficacy of an anti-MUC16/anti-CD3 bispecific antibody in combination with 4-1 BB co-stimulation was first evaluated in a xenogeneic tumor model. For the xenogeneic model, ascites cells from the OVCAR-3/Luc cell line previously passaged in vivo (Day 0) were injected intraperitoneally into NSG (Nod scid gamma) mice thirteen days after engraftment with human PBMCs. Mice, five in each group, were treated intraperitoneally with 12.5 ug/mouse of MUC16×CD3 or CD3-binding control alone or in combination with 100 ug/mouse of anti-human 4-1BB (clone LOB12.3 from BioXcell, Lebanon, NH) on Days 5 and 8. Tumor burden was assessed by Bioluminescence Imaging (BLI; measuring luminescence) on Days 4, 8, 12, 15, 20 and 25 post tumor implantations.

Calculation of xenograft tumor growth and inhibition: BLI was used to measure tumor burden. Mice were injected IP with 150 mg/kg (as determined by body weights at the start of the experiment) of the luciferase substrate D-luciferin suspended in PBS. Ten minutes after dosing, BLI imaging of the mice was performed under isoflurane anesthesia using the Xenogen IVIS system. Image acquisition was carried out with the field of view at D, subject height of 1.5 cm, and medium binning level for 0.5-min exposure time. BLI signals were extracted using Living Image software. Regions of interest were drawn around each tumor mass and photon intensities were recorded as $p/s/cm^2/sr$. Statistical analysis was performed using GraphPad Prism software (Version 6). Statistical significance for the BLI results was determined using an unpaired nonparametric Mann-Whitney t-test.

Data shown is tumor burden as assessed by BLI on Day 4 post tumor implantation (Table 2 and FIG. 1). Statistical significance was determined using unpaired nonparametric Mann-Whitney t-tests. There was no significant difference in tumor burden between groups on Day 4 (showing all groups had similar tumor burden at start of study).

TABLE 2

Bioluminescence on Day 4 Post Tumor Implantation in OVCAR-3 Model

| Antibody (ug) | Avg Radiance [p/s/cm²/sr] 4 days post-implantation (median ± SEM) |
|---|---|
| CD3-binding Control (12.5) | 1.51e+05 ± 2.81e+04 |
| MUC16XCD3 (12.5) | 1.5e+05 ± 1.05e+04 |
| CD3-binding Control (12.5) + anti-4-1BB (100) | 1.03e+05 ± 1.59e+04 |
| MUC16XCD3 (12.5) + anti-4-1BB (100) | 1.02e+05 ± 3.11e+04 |

Table 3 shows tumor burden as assessed by BLI on Day 25 post tumor implantation (see also FIG. 2). Statistical significance was determined using unpaired nonparametric Mann-Whitney t-tests. Groups were compared to the CD3-binding control (* p=0.0159 for MUC16×CD3, ** p<0.0079 for MUC16×CD3 and anti-4-1BB combination). MUC16×CD3 and anti-4-1BB combination was also compared to MUC16×CD3 alone (#p=0.0159). MUC16×CD3 significantly reduced tumor burden at 12.5 ug relative to tumor burden after treatment with CD3-binding control, and addition of anti-4-1BB enhanced the anti-tumor efficacy over that of MUC16×CD3 alone.

TABLE 3

Bioluminescence on Day 25 Post Tumor Implantation in OVCAR-3 Model

| Antibody (ug) | Avg Radiance [p/s/cm²/sr] 25 days post-implantation (median ± SEM) |
|---|---|
| CD3-binding Control (12) | 7.71e+06 ± 1.07e+06 |
| MUC16XCD3 (12) | 7.44e+03 ± 3.11e+03 |
| CD3-binding Control (12) + anti-4-1BB (100) | 6.65e+06 ± 1.06e+06 |
| MUC16XCD3 (12) + anti-4-1BB (100) | 1.47e+03 ± 1.11e+02 |

Example 3: MUC16×CD3+4-1BB Treatment in Syngeneic Ascites Model

To examine efficacy in an immune-competent model, the murine CD3 gene was replaced with human CD3 and a portion of the mouse MUC16 gene was replaced with the human sequence. The resulting mice have T cells which express human CD3 and the mice express a chimeric MUC16 molecule containing a portion of human MUC16 where MUC16×CD3 bispecific antibody binds. Mice were implanted with ID8-VEGF/huMUC16 cells (a murine ovarian tumor cell line engineered to express the portion of human MUC16) intraperitoneally and treatment with antibodies was intravenous and began on Day 3 post tumor implantation. Mice were administered either MUC16×CD3 (1 mg/kg IV) or CD3-binding control (1 mg/kg IV) with isotype control on days 3, 6 and 10 post implantation or with anti-mouse 4-1 BB (2.5 mg/kg IV) on day 3 post implantation followed by two additional doses of MUC16×CD3 (1 mg/kg IV) on days 6 and 10. There were 8-12 mice in each group. Mice were sacrificed when they had a weight-gain of more than 30% due to ascites-induced abdominal distension. Statistical significance was determined using the Gehan-Breslow-Wilcoxon method.

MUC16×CD3 treatment significantly increased median survival time in the ID8-VEGF/huMUC16 ascites model and addition of 4-1 BB co-stimulation allowed survival of several mice. For statistical analysis, groups were compared to the CD3-binding control (p=0.0026 for MUC16×CD3, ** p<0.0001 for MUC16×CD3 with anti-4-1 BB). In addition, to determine whether addition of anti-4-1 BB had any beneficial outcome over MUC16×CD3 alone, anti-4-1 BB was compared to MUC16×CD3 alone (#p=0.0168). MUC16×CD3 increased the median survival time over the CD3-binding control group as well as the % of mice surviving (from 0 to 27%). The median survival time for the MUC16×CD3+anti-4-1 BB combination group could not be defined since more than 50% of mice survived. The total survival of the combination treated group was 55% (Table 4 and FIG. 3). These effects were seen without any significant weight loss during the dosing period, which was used as a read-out for toxicity (Table 5 and FIG. 4).

TABLE 4

Median Survival in ID8-VEGF/huMUC16 Model

| Group name | D 3 Antibody (mg/kg) | D 6 Antibody (mg/kg) | D 10 Antibody (mg/kg) | Median Survival (Days) | Tumor free/ total mice | % survival |
|---|---|---|---|---|---|---|
| Control | CD3-binding control (1) + isotype control (5) | CD3-binding control (1) + isotype control (5) | CD3-binding control (1) + isotype control (5) | 35 | 0/11 | 0 |

TABLE 4-continued

Median Survival in ID8-VEGF/huMUC16 Model

| Group name | D 3 Antibody (mg/kg) | D 6 Antibody (mg/kg) | D 10 Antibody (mg/kg) | Median Survival (Days) | Tumor free/ total mice | % survival |
|---|---|---|---|---|---|---|
| CD3 bispecific | MUC16XCD3 (1) + isotype control (5) | MUC16XCD3 (1) + isotype control (5) | MUC16XCD3 (1) + isotype control (5) | 47 | 3/11 | 27 |
| Anti-4-1BB | CD3-binding control (1) + anti-4-1BB (2.5) | CD3-binding control (1) + isotype control (5) | CD3-binding control (1) + isotype control (5) | 47 | 1/7 | 14 |
| CD3 bispecific + anti-4-1BB | MUC16XCD3 (1) + anti-4-1BB (2.5) | MUC16XCD3 (1) + isotype control (5) | MUC16XCD3 (1) + isotype control (5) | undefined | 5/9 | 55 |

TABLE 5

Weight change at Day 10 and Day 31 post implantation (before first death in study) in ID8-VEGF/huMUC16 Model

| | Day 12 | | | Day 31 | | |
|---|---|---|---|---|---|---|
| Group name | Mean weight change | SD | Statistical analysis compared to group 1 (two-way ANOVA) | Mean weight change | SD | Statistical analysis compared to group 1 (two-way ANOVA) |
| Control | 2.7 | 2.6 | | 16.4 | 10.0 | |
| CD3 bispecific | 3.1 | 3.0 | NS (1.0) | 10.0 | 5.8 | * (0.01) |
| Anti-4-1BB | 0.42 | 3.5 | NS (0.73) | 8.7 | 14.0 | ** (0.0035) |
| CD3 bispecific + anti-4-1BB | 3.4 | 3.2 | NS (0.99) | 5.7 | 4.3 | **** (<0.0001) |

In addition to initial anti-tumor efficacy, the mice were also assessed for any memory response and epitope spreading. On day 116 post implantation, the tumor-free mice were re-challenged by subcutaneously implanting parental ID8-VEGF. Nine naïve mice were also included as a control for tumor growth. Data shown is the number of mice tumor free after re-challenge (Table 6). Two of the three mice treated with MUC16×CD3 were able to clear a secondary challenge with the parental tumor line not expressing MUC16. In addition, all of the 5 mice treated with MUC16×CD3+anti-4-1 BB combination were able to clear tumors. This shows that a memory response was able to form in the presence of these two treatment regimens.

TABLE 6

Memory Response in ID8-VEGF/huMUC16 Model

| Treatment group from initial ascites study | Tumor free mice/total |
|---|---|
| Naïve control mice not previously in study | 0/9 |
| Mice previously treated with MUC16XCD3 (1) + isotype control (5) | 2/3 |
| Mice previously treated with MUC16XCD3 (1) + anti-4-1BB (2.5) | 5/5 |

Example 4: MUC16×CD3+4-1BB Treatment in ID8-VEGF/huMUC16 Model

Like Example 3, mice expressing human CD3 in place of mouse CD3 and a chimeric MUC16 molecule were implanted with the murine ovarian tumor line expressing a portion of human MUC16. Three dosing regimens were tested, with 9-10 mice per treatment in each dosing regimen:

A) Combination of either MUC16×CD3 (1 mg/kg i.v.) or CD3-binding control (1 mg/kg i.v.) with either isotype control (2.5 mg/kg IV) or anti-mouse 4-1 BB (2.5 mg/kg i.v.) on days 3, 7, and 10 post-implantation.

B) One dose of combination of MUC16×CD3 (1 mg/kg i.v.) plus anti-mouse 4-1 BB (2.5 mg/kg i.v.) on day 3 post implantation followed by doses of MUC16× CD3(1 mg/kg i.v.) on days 7 and 10 post-implantation.

C) One dose of combination of MUC16×CD3 (1 mg/kg i.v.) or CD3-binding control (1 mg/kg i.v.) plus anti-mouse 4-1 BB (2.5 mg/kg i.v.) day 3 post implantation with no further treatments.

Data shown is median survival to day 67 post tumor implantation. See Table 7 and FIG. 5. Mice were sacrificed before day 67 if they had weight-gain of more than 30% due to ascites-induced abdominal distension. Statistical significance was determined using the Gehan-Breslow-Wilcoxon method. For statistical analysis, groups were compared to the CD3-binding control (p=0.002 for MUC16×CD3, ** p<0.0001 for all three groups consisting of MUC16× CD3 and anti-4-1 BB in combination). In addition, to determine whether combination with anti-4-1 BB had any beneficial outcome over MUC16×CD3 alone, all groups were compared to this group (#p=0.011 for Gp4 (3 doses of CD3 bispecific+3 doses of anti-4-1BB), #p=0.027 for Gp5 (3 doses of CD3 bispecific+only 1 dose of anti-4-1 BB), #p=0.011 for Gp7 (one dose of CD3 bispecific+anti-4-1BB)). Mice treated with MUC16×CD3+anti-4-1 BB demonstrated efficacy and long-term survival. These effects were seen without any significant weight loss during the dosing period, which was used as a read-out for toxicity (Table 8 and FIG. 6).

TABLE 7

Median Survival in ID8-VEGF/huMUC16 Model

| Grp | Group name | Day 3 Antibody (mg/kg) | Day 7 Antibody (mg/kg) | Day 10 Antibody (mg/kg) | Median Survival (Days) | Tumor free/ total mice |
|---|---|---|---|---|---|---|
| 1 | 3 doses of CD3 control | CD3-binding control (1) + isotype control(2.5) | CD3-binding control (1) + isotype control(2.5) | CD3-binding control (1) + isotype control(2.5) | 41 | 0/9 |
| 2 | 3 doses of bispecific | MUC16XCD3 (1) + isotype control (2.5) | MUC16XCD3 (1) + isotype control (2.5) | MUC16XCD3 (1) + isotype control (2.5) | 51 | 0/9 |
| 3 | 3 doses of anti-4-1BB | CD3-binding control (1) + anti-4-1BB (2.5) | CD3-binding control (1) + anti-4-1BB (2.5) | CD3-binding control (1) + anti-4-1BB (2.5) | 44 | 2/10 |
| 4 | 3 doses of bispecific + 3 doses of anti-4-1BB | MUC16XCD3 (1) + anti-4-1BB (2.5) | MUC16XCD3 (1) + anti-4-1BB (2.5) | MUC16XCD3 (1) + anti-4-1BB (2.5) | undefined | 9/10 |
| 5 | 3 doses of bispecific + only 1 dose of anti-4-1BB | MUC16XCD3 (1) + anti-4-1BB (2.5) | MUC16XCD3 (1) + isotype control (2.5) | MUC16XCD3 (1) + isotype control (2.5) | undefined | 8/10 |
| 6 | One dose of anti-4-1BB | CD3-binding control (1) + anti-4-1BB (2.5)1 | | | 43.5 | 0/10 |
| 7 | One dose of bispecific + anti-4-1BB | MUC16XCD3 (1) + anti-4-1BB (2.5) | | | undefined | 9/10 |

TABLE 8

Weight change at Day 12 and Day 30 post implantation (before first death in study) in ID8-VEGF/huMUC16 Model

| | | Day 12 | | | Day 30 | | |
|---|---|---|---|---|---|---|---|
| Grp | Group name | Mean weight change | SD | Statistical analysis compared to group 1 (two-way ANOVA) | Mean weight change | SD | Statistical analysis compared to group 1 (two-way ANOVA) |
| 1 | CD3 control | −2.9 | 2.9 | | 3.6 | 5.6 | |
| 2 | CD3 bispecific | −5.3 | 3.1 | NS (0.75) | −0.8 | 4.9 | NS (0.073) |
| 3 | 3 doses of anti-4-1BB | −3.1 | 1.9 | NS (1.0) | 0.8 | 4.4 | NS (0.49) |
| 4 | 3 doses of CD3 bispecific + 3 doses of anti-4-1BB | −5.9 | 2.4 | NS (0.44) | −2.5 | 2.0 | ** (0.001) |
| 5 | 3 doses of CD3 bispecific + only 1 dose of anti-4-1BB | −4.2 | 2.0 | NS (0.98) | −1.9 | 3.5 | ** (0.006) |
| 6 | One dose of anti-4-1BB | −3.8 | 3.0 | NS (1.0) | 2.5 | 13.4 | NS (0.99) |
| 7 | One dose of CD3 bispecific + anti-4-1BB | −4.2 | 1.9 | NS (0.98) | −2.6 | 2.9 | *** (0.001) |

Conclusions:

A CD3-bispecific antibody targeting tumor antigen MUC16 (MUC16) shows preclinical efficacy in multiple mouse models. MUC16×CD3 combined with anti-4-1 BB achieved durable anti-tumor activity resulting in long term survival of mice, demonstrating that co-stimulation can enhance the potency of MUC16×CD3-bispecific antibodies against advanced solid tumors. These effects were seen in the absence of weight loss in the mice; weight-loss was used as a readout of toxicity. In addition, a memory response was elicited upon reinjection of tumor cells lacking the MUC16 antigen, demonstrating a robust anti-tumor response that was not dependent on response to the MUC16 antigen.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of treating a cancer that expresses MUC16 or inhibiting the growth of a MUC16-expressing tumor comprising administering to a subject in need thereof a therapeutically effective amount each of (a) an anti-CD3/anti-MUC16 bispecific antigen-binding molecule; and (b) a 4-1BB agonist.

2. The method of claim 1, wherein the cancer is selected from the group consisting of breast cancer, ovarian cancer, corneal cancer, pancreatic cancer, endometrial cancer, fallopian tube cancer, mesothelioma, non-small cell lung cancer, intrahepatic cholangiocarcinoma-mass forming type, uterine cancer, cervical cancer, gastric cancer, or colorectal carcinoma.

3. The method of claim 2, wherein the cancer is ovarian cancer.

4. The method of claim 2, wherein the cancer is breast cancer.

5. The method of claim 1, wherein the anti-CD3/anti-MUC16 bispecific antibody and the 4-1BB agonist are administered separately.

6. The method of claim 1, wherein the anti-CD3/anti-MUC16 bispecific antibody and the 4-1BB agonist are co-administered.

7. The method of claim 1, wherein the anti-CD3/anti-MUC16 bispecific antibody is administered prior to, concurrent with or after the 4-1BB agonist.

8. The method of claim 7, wherein the anti-CD3/anti-MUC16 bispecific antibody is administered prior to the 4-1BB agonist.

9. The method of claim 7, wherein the anti-CD3/anti-MUC16 bispecific antibody is administered the same day as the 4-1BB agonist.

10. The method of claim 1, wherein the anti-CD3/anti-MUC16 bispecific antibody is administered in combination with the 4-1BB agonist.

11. The method of claim 1, wherein the 4-1BB agonist is selected from a small molecule or an antibody.

12. The method of claim 11, wherein the 4-1BB agonist is an antibody selected from the group consisting of urelumab and utomilumab.

13. The method of claim 1, wherein the bispecific antigen-binding molecule comprises a first antigen-binding domain that specifically binds CD3 and comprises a HCVR-1 amino acid sequence of SEQ ID NO: 2, a second antigen-binding domain that specifically binds MUC16 and comprises a HCVR-2 amino acid sequence of SEQ ID NO: 1, and a common light chain variable region (LCVR) amino acid sequence of SEQ ID NO: 3.

14. The method of claim 1, wherein the tumor volume is decreased relative to tumor volume in a subject administered the anti-CD3/anti-MUC16 bispecific antigen-binding molecule in the absence of a 4-1BB agonist.

15. The method of claim 1, wherein tumor free survival time is increased in the subject relative to tumor free survival time in a subject administered the anti-CD3/anti-MUC16 bispecific antigen-binding molecule in the absence of a 4-1BB agonist.

16. The method of claim 15, wherein the increase in tumor free survival time occurs without weight loss in the subject.

17. The method of claim 1, wherein subsequent exposure to tumor cells elicits a memory response in the subject treated with the anti-CD3/anti-MUC16 bispecific antigen-binding molecule in the presence of a 4-1BB agonist.

* * * * *